United States Patent
Samusik et al.

(10) Patent No.: US 10,006,082 B2
(45) Date of Patent: *Jun. 26, 2018

(54) ON-SLIDE STRAINING BY PRIMER EXTENSION

(71) Applicant: The Board of Trustees of the Leland Stanford Junior University, Stanford, CA (US)

(72) Inventors: Nikolay Samusik, Mountain View, CA (US); Garry P. Nolan, Redwood City, CA (US); Yury Goltsev, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/832,627

(22) Filed: Dec. 5, 2017

(65) Prior Publication Data

US 2018/0119208 A1    May 3, 2018

Related U.S. Application Data

(63) Continuation of application No. 14/560,921, filed on Dec. 4, 2014, now Pat. No. 9,909,167.

(60) Provisional application No. 62/015,799, filed on Jun. 23, 2014.

(51) Int. Cl.
*C12Q 1/68* (2018.01)
*C12Q 1/6818* (2018.01)
*C12Q 1/6804* (2018.01)

(52) U.S. Cl.
CPC ......... *C12Q 1/6818* (2013.01); *C12Q 1/6804* (2013.01)

(58) Field of Classification Search
None
See application file for complete search history.

(56) References Cited

U.S. PATENT DOCUMENTS

| | | | |
|---|---|---|---|
| 5,068,178 A * | 11/1991 | Nowinski | G01N 33/56966 435/34 |
| 6,531,283 B1 * | 3/2003 | Kingsmore | C12Q 1/6804 435/6.12 |
| 6,743,592 B1 | 6/2004 | Greene et al. | |
| 7,341,831 B2 | 3/2008 | Greene et al. | |
| 7,361,464 B2 | 4/2008 | Greene et al. | |
| 7,846,746 B2 | 12/2010 | Nollau et al. | |
| 8,088,715 B2 | 1/2012 | Bodmer et al. | |
| 8,241,858 B2 | 8/2012 | Eberwine | |
| 8,305,579 B2 | 11/2012 | Treynor et al. | |
| 8,309,306 B2 | 11/2012 | Nolan et al. | |
| 8,445,411 B2 | 5/2013 | Bodmer et al. | |
| 8,530,156 B2 | 9/2013 | Church et al. | |
| 8,658,381 B2 | 2/2014 | Mansson et al. | |
| 8,753,824 B2 | 6/2014 | Papin et al. | |
| 8,946,389 B2 | 2/2015 | Gao et al. | |
| 9,376,717 B2 | 6/2016 | Gao et al. | |
| 9,625,387 B2 | 4/2017 | Demos et al. | |
| 2004/0023271 A1 | 2/2004 | Kurn | |
| 2005/0186572 A1 | 8/2005 | Egholm et al. | |
| 2007/0020650 A1 | 1/2007 | Kahvejian | |
| 2007/0026430 A1 | 2/2007 | Andersen et al. | |
| 2007/0148645 A1 | 6/2007 | Hoser | |
| 2008/0317325 A1 | 12/2008 | Ortyn et al. | |
| 2010/0075307 A1 | 3/2010 | Belyaev | |
| 2010/0120043 A1 | 5/2010 | Sood et al. | |
| 2010/0261781 A1 | 10/2010 | Gmeiner | |
| 2011/0033846 A1 | 2/2011 | Dattagupta | |
| 2011/0046359 A1 | 2/2011 | Lee et al. | |
| 2011/0086780 A1 | 4/2011 | Colston, Jr. et al. | |
| 2011/0092381 A1 * | 4/2011 | Sood | C12Q 1/6816 506/9 |
| 2011/0136116 A1 | 6/2011 | Barany et al. | |
| 2012/0028242 A1 | 2/2012 | Heyduk et al. | |
| 2012/0258880 A1 | 10/2012 | Schwartz et al. | |
| 2013/0172213 A1 | 7/2013 | Oliphant et al. | |
| 2013/0323729 A1 | 12/2013 | Landegren et al. | |
| 2014/0080126 A1 | 3/2014 | Cantor et al. | |
| 2015/0004598 A1 | 1/2015 | Gao et al. | |
| 2015/0005188 A1 | 1/2015 | Levner et al. | |

(Continued)

FOREIGN PATENT DOCUMENTS

| EP | 1270738 | 1/2003 |
|---|---|---|
| EP | 1851331 B1 | 2/2016 |

(Continued)

OTHER PUBLICATIONS

Dhillon et al., "Homogeneous and digital proximity ligation assays for the detection of Clostridium difficile toxins A and B", Biomolecular Detection and Quantification, 2016, 10:2-8.
Shahi et al., "Abseq: Ultrahigh-throughput single cell protein profiling with droplet microfluidic barcoding", Scientific Reports, 2017, 7:44447, DOI: 10.1038/srep44447.
Zhang et al., "Protein quantification from complex protein mixtures using a proteomics methodology with single-cell resolution", PNAS, 2001, 98(10): 5497-5502.
Zhang et al., "A sensitive and high-throughput assay to detect low-abundance proteins in serum", Nature Medicine, 2006, 12(4): 473-477.
Flanigon et al., "Multiplex protein detection with DNA readout via mass spectrometry" N Biotechnol. (2013) 30(2):153-158.
Kazane S.A. et al., "Site-specfic DNA-antibody conjugates for specific and sensitive immuno-PCR" Procl Natl Acad Sci (2012) 109(10):3731-6.

(Continued)

*Primary Examiner* — Aaron A Priest
(74) *Attorney, Agent, or Firm* — James S. Keddie; Bozicevic, Field & Francis LLP

(57) ABSTRACT

A method for analyzing planar sample is provided. In some cases the method comprises: (a) incubating the planar sample with a capture agent that is linked to an oligonucleotide, wherein the capture agent specifically binds to complementary sites in the planar sample; (b) reading a fluorescent signal caused by extension of a primer that is hybridized to the oligonucleotide, using fluorescence microscopy. Several implementations of the method, and multiplexed versions of the same, are also provided.

20 Claims, 15 Drawing Sheets
(13 of 15 Drawing Sheet(s) Filed in Color)

(56) References Cited

U.S. PATENT DOCUMENTS

| | | | |
|---|---|---|---|
| 2015/0309028 A1* | 10/2015 | Jordan | C07K 16/3046 435/7.92 |
| 2015/0368697 A1 | 12/2015 | Samusik et al. | |
| 2016/0161472 A1 | 6/2016 | Jungmann et al. | |
| 2016/0169903 A1 | 6/2016 | Dai et al. | |
| 2016/0319328 A1 | 11/2016 | Yin et al. | |
| 2016/0346330 A1 | 12/2016 | Sussman et al. | |
| 2017/0009278 A1 | 1/2017 | Söderberg et al. | |
| 2017/0038391 A1 | 2/2017 | Lara Gutierrez et al. | |
| 2017/0137864 A1 | 5/2017 | Yin et al. | |
| 2017/0151569 A1 | 6/2017 | Handique et al. | |
| 2017/0349949 A1 | 12/2017 | Kolb | |

FOREIGN PATENT DOCUMENTS

| | | |
|---|---|---|
| WO | WO2008/052774 | 5/2008 |
| WO | WO2012058638 | 5/2012 |
| WO | WO2012071428 | 5/2012 |
| WO | WO 2012134602 | 10/2012 |
| WO | WO2013/113699 | 8/2013 |
| WO | WO 2013/188756 | 12/2013 |
| WO | WO 2014/200767 | 12/2014 |
| WO | WO2015017586 | 2/2015 |
| WO | WO 2015/052287 | 4/2015 |
| WO | WO 2015/200139 | 12/2015 |
| WO | WO2015188839 | 12/2015 |
| WO | WO 2015200139 | 12/2015 |

OTHER PUBLICATIONS

Byers et al., "Semiautomated Multiplexed Quantum Dot-Based in Situ Hybridization and Spectral Deconvolution", Journal of Molecular Diagnostics, 2007, 9(1): 20-29.

Chan et al., "Luminescent quantum dots for multiplexed biological detection and imaging", Current Opinion in Biotechnology, 2002, 13:40-46.

Englert et al., "Layered Expression Scanning: Rapid Molecular Profiling of Tumor Samples", Cancer Research, 2000, 60: 1526-1530.

Flor et al., "DNA-Directed Assembly of Antibody-Fluorophore Conjugates for Quantitative Multiparametric Flow Cytometry", Chembiochem, 2013, 15(2): 267-275.

Furuya et al., "A Novel Technology Allowing Immunohistochemical Staining of a Tissue Section with 50 Different Antibodies in a Single Experiment", Journal of Histochemistry & Cytochemistry, 2004, 52(2): 205-210.

Guo et al., "Multispectral labeling of antibodies with polyfluorophores on a DNA backbone and application in cellular imaging", PNAS, 2011, 108(9): 3493-3498.

Han et al., "An Approach to Multiplexing an Immunosorbent Assay with Antibody-Oligonucleotide Conjugates", Bioconjugate Chem., 2010, 21: 2190-2196.

Huang et al., "Comparison and Optimization of Multiplexed Quantum Dot-Based Immunohistofluorescence", Nano Res, 2010, 3: 61-68.

Larson et al., "Analytical Validation of a Highly Quantitative, Sensitive, Accurate, and Reproducible Assay (HERmark) for the Measurement of HER2 Total Protein and HER2 Homodimers in FFPE Breast Cancer Tumor Specimens", Pathology Research International, 2010, Article ID 814176, 14 pages.

Lundberg et al., "Homogeneous antibody-based proximity extension assays provide sensitive and specific detection of low-abundant proteins in human blood", Nucleic Acids Research, 2011, 39(15): e102.

Niemeyer et al., "Detecting antigens by quantitative immuno-PCR", Nature Protocols, 2007, 2(8): 1918-1930.

Saiki et al., "Analysis of enzymatically amplified β-globin and HLA-DQα DNA with allele-specific oligonucleotide probes", Nature, 1986, 324: 163-166.

Tran et al., "A Universal DNA-Based Protein Detection System", Journal of the American Chemical Society, 2013, 135(38): 14008-14011.

True et al., "Quantum Dots for Molecular Pathology", Journal of Molecular Diagnostics, 2007, 9(1): 7-11.

Ullal et al., "Cancer Cell Profiling by Barcoding Allows Multiplexed Protein Analysis in Fine-Needle Aspirates", Science Translational Medicine, 2014, 6(219): 219ra9.

Wahlby et al., "Sequential Immunofluorescence Staining and Image Analysis for Detection of Large Numbers of Antigens in Individual Cell Nuclei", Cytometry, 2002, 47:32-41.

Zrazhevskiy et al., "Quantum dot imaging platform for single-cell molecular profiling", Nat Commun. 2013 4: 1-12.

* cited by examiner

A

"Labeling" base

↓ (SEQ ID NO: 5)

TTCTAgggggggggggggGTCGTCAAGATGCTACCGTTCAGGz
⎵⎵⎵⎵⎵⎵⎵⎵⎵⎵⎵⎵⎵⎵⎵   CAGCTACGCCTGAACGTAGGAAGTCCGGTAGGGATA
"Walking" bases           (SEQ ID NO: 6)

B

"Labeling" base

↓ (SEQ ID NO: 7)

TTCTAacgatctagtcgGTCGTCAAGATGCTACCGTTCAGGz
⎵⎵⎵⎵⎵⎵⎵⎵⎵⎵⎵⎵⎵   CAGCTACGCCTGAACGTAGGAAGTCCGGTAGGGATA
"Walking" bases         (SEQ ID NO: 8)

C

"Labeling" base

↓ (SEQ ID NO: 9)

TTCTActctctctctctGTCGTCAAGATGCTACCGTTCAGGz
⎵⎵⎵⎵⎵⎵⎵⎵⎵⎵⎵⎵⎵   CAGCTACGCCTGAACGTAGGAAGTCCGGTAGGGATA
"Walking" bases         (SEQ ID NO: 10)

D

"Labeling" base

↘ T-strech (kT)  C-strech (nC)
                ↙        ↙  (SEQ ID NO: 11)

TTCTActccttCcTctGTCGTCAAGATGCTACCGTTCAGGz
⎵⎵⎵⎵⎵⎵⎵⎵⎵⎵⎵⎵⎵   CAGCTACGCCTGAACGTAGGAAGTCCGGTAGGGATA
"Walking" bases         (SEQ ID NO: 12)

Ab1-3′-GAACCGGTGAGTGGGATCGTGACCGAGCGAGATA (SEQ ID NO: 68)

Ab1-3′-GAACCGGTGAGTGGGATCGTGACCGAGCGAGATA (SEQ ID NO: 69)
      5′-GCACTGGCTCGCTCTA (SEQ ID NO: 70)

Ab1-3′-GAACCGGTGAGTGGGATCGTGACCGAGCGAGATA (SEQ ID NO: 71)
      5′-GCACTGGCTCGCTCTAU— (SEQ ID NO: 72)

Ab1-3′-GAACCGGTGAGTGGGATCGTGACCGAGCGAGATA (SEQ ID NO: 73)
      5′-GCACTGG (SEQ ID NO: 74)

B

Ab1-3′-GAACCGGTGAGTGGGATCGTGACCGAGCGAGATAC (SEQ ID NO: 75)
      5′-GCACTGGCTCGCTCTAU— (SEQ ID NO: 76)

Ab2-3′-GAACCGGTGAGTGGGATCGTGACCGGACCTGTAAC (SEQ ID NO: 77)
      5′-GCACTGG 
      (SEQ ID NO: 78)

Ab3-3′-GAACCGGTGAGTGGGATCGTGACCAGTGACTGAAC (SEQ ID NO: 79)
      5′-GCACTGG
      (SEQ ID NO: 80)

FIGS. 9A-9B

```
                                          (SEQ ID NO: 81)
Ab1- 3' NNNNNNNNNNNNNNNNNNNCGCCGTGCTCGCATGCA
                      5' -GCGGCACGAGCGTACGU
                         (SEQ ID NO: 82)
                                          (SEQ ID NO: 83)
Ab2- 3' NNNNNNNNNNNNNNNNNNNCGCCGTGCTCGCGTCCA
                      5' -GCGGCACGAGCG
                         (SEQ ID NO: 84)
                                          (SEQ ID NO: 85)
Ab3- 3' NNNNNNNNNNNNNNNNNNNCGCCGTGCTCGCTACGA
                      5' -GCGGCACGAGCG
                         (SEQ ID NO: 86)
```

FIG. 10

SEQUENCE LISTING

```
<160> NUMBER OF SEQ ID NOS: 92

<210> SEQ ID NO 1
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is uridine
<220> FEATURE:
<221> NAME/KEY: misc_feature
<222> LOCATION: (5)..(5)
<223> OTHER INFORMATION: n is uridine
<220> FEATURE:
<221> NAME/KEY: misc_feature
<222> LOCATION: (9)..(9)
<223> OTHER INFORMATION: n is uridine
<220> FEATURE:
<221> NAME/KEY: misc_feature
<222> LOCATION: (13)..(13)
<223> OTHER INFORMATION: n is uridine

<400> SEQUENCE: 1
naaanaaana aan                                                    13

<210> SEQ ID NO 2
<211> LENGTH: 13
<212> TYPE: DNA
```

```
<213> ORGANISM: Artificial Sequence
<220> FEATURE:
<223> OTHER INFORMATION: Synthetic oligonucleotide

<400> SEQUENCE: 2
atttatttat tta                                                          13

<210> SEQ ID NO 3
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is uridine
<220> FEATURE:
<221> NAME/KEY: misc_feature
<222> LOCATION: (5)..(5)
<223> OTHER INFORMATION: n is uridine
<220> FEATURE:
<221> NAME/KEY: misc_feature
<222> LOCATION: (11)..(11)
<223> OTHER INFORMATION: n is uridine

<400> SEQUENCE: 3
naacnaacaa n                                                            11

<210> SEQ ID NO 4
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 4
attgttattg tta                                                          13

<210> SEQ ID NO 5
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: c is dideoxycytidine

<400> SEQUENCE: 5
ttctaggggg ggggggggtc gtcaagatgc taccgttcag gc                          42

<210> SEQ ID NO 6
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 6
atagcgctac cctgaacggt agcatcttga cgac                                   34

<210> SEQ ID NO 7
<211> LENGTH: 42
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: c is dideoxycytidine

<400> SEQUENCE: 7
ttctaacgat ctagtcggtc gtcaagatgc taccgttcag gc                    42

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 8
atagcgctac gcctgaacgg tagcatcttg acgac                             35

<210> SEQ ID NO 9
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 9
ttctactctc tctctctgtc gtcaagatgc taccgttcag g                      41

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 10
atagcgctac gcctgaacgg tagcatcttg acgac                             35

<210> SEQ ID NO 11
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 11
ttctactcct ttcctctgtc gtcaagatgc taccgttcag g                      41

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
```

<223> OTHER INFORMATION: linked to an antibody at the 5' end

<400> SEQUENCE: 12
atagcgctac gcctgaacgg tagcatcttg acgac                                35

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(5)
<223> OTHER INFORMATION: c is dideoxycytidine

<400> SEQUENCE: 13
atagcgctac gcctgaacgg tagcatcttg acgac                                35

<210> SEQ ID NO 14
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(27)
<223> OTHER INFORMATION: n is a, c, g, or t
<220> FEATURE:
<221> NAME/KEY: misc_feature
<222> LOCATION: (52)..(52)
<223> OTHER INFORMATION: c is dideoxycytidine

<400> SEQUENCE: 14
tttttannnn nnnnnnnnnn nnnnnnngtc gtcaagatgc taccgttcag gc             52

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 15
atagcgctac gcctgaacgg tagcatcttg acgac                                35

<210> SEQ ID NO 16
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(28)
<223> OTHER INFORMATION: n is a, c, g, or t
<220> FEATURE:
<221> NAME/KEY: misc_feature

```
<222> LOCATION: (53)..(53)
<223> OTHER INFORMATION: c is dideoxycytidine

<400> SEQUENCE: 16
tttttacnnn nnnnnnnnnn nnnnnnnngt cgtcaagatg ctaccgttca ggc        53

<210> SEQ ID NO 17
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 17
atagcgctac gcctgaacgg tagcatcttg acgac                              35

<210> SEQ ID NO 18
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(29)
<223> OTHER INFORMATION: n is a, c, g, or t
<220> FEATURE:
<221> NAME/KEY: misc_feature
<222> LOCATION: (54)..(54)
<223> OTHER INFORMATION: c is dideoxycytidine

<400> SEQUENCE: 18
tttttactnn nnnnnnnnnn nnnnnnnnng tcgtcaagat gctaccgttc aggc         54

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(5)
<223> OTHER INFORMATION: c is dideoxycytidine

<400> SEQUENCE: 19
atagcgctac gcctgaacgg tagcatcttg acgac                              35

<210> SEQ ID NO 20
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(27)
<223> OTHER INFORMATION: n is a, c, g, or t
<220> FEATURE:
```

```
<221> NAME/KEY: misc_feature
<222> LOCATION: (52)..(52)
<223> OTHER INFORMATION: c is dideoxycytidine

<400> SEQUENCE: 20
tttttannnn nnnnnnnnnn nnnnnnngtc gtcaagatgc taccgttcag gc          52

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 21
atagcgctac gcctgaacgg tagcatcttg acgac                             35

<210> SEQ ID NO 22
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(28)
<223> OTHER INFORMATION: n is a, c, g, or t
<220> FEATURE:
<221> NAME/KEY: misc_feature
<222> LOCATION: (53)..(53)
<223> OTHER INFORMATION: c is dideoxycytidine

<400> SEQUENCE: 22
tttttacnnn nnnnnnnnnn nnnnnnnngt cgtcaagatg ctaccgttca ggc          53

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 23
atagcgctac gcctgaacgg tagcatcttg acgac                             35

<210> SEQ ID NO 24
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(29)
<223> OTHER INFORMATION: n is a, c, g, or t
```

<220> FEATURE:
<221> NAME/KEY: misc_feature
<222> LOCATION: (54)..(54)
<223> OTHER INFORMATION: c is dideoxycytidine

<400> SEQUENCE: 24 ttttactnn nnnnnnnnnn nnnnnnnnng tcgtcaagat gctaccgttc aggc    54

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 25
atagcgctac gcctgaacgg tagcatcttg acgac    35

<210> SEQ ID NO 26
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(27)
<223> OTHER INFORMATION: n is a, c, g, or t
<220> FEATURE:
<221> NAME/KEY: misc_feature
<222> LOCATION: (52)..(52)
<223> OTHER INFORMATION: c is dideoxycytidine

<400> SEQUENCE: 26
tttttannnn nnnnnnnnnn nnnnnnngtc gtcaagatgc taccgttcag gc    52

<210> SEQ ID NO 27
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 27
atagcgctac gcctgaacgg tagcatcttg acgac    35

<210> SEQ ID NO 28
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(28)

<223> OTHER INFORMATION: n is a, c, g, or t
<220> FEATURE:
<221> NAME/KEY: misc_feature
<222> LOCATION: (53)..(53)
<223> OTHER INFORMATION: c is dideoxycytidine

<400> SEQUENCE: 28
tttttacnnn nnnnnnnnnn nnnnnnnngt cgtcaagatg ctaccgttca ggc    53

<210> SEQ ID NO 29
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 29
atagcgctac gcctgaacgg tagcatcttg acgac    35

<210> SEQ ID NO 30
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(29)
<223> OTHER INFORMATION: n is a, c, g, or t
<220> FEATURE:
<221> NAME/KEY: misc_feature
<222> LOCATION: (54)..(54)
<223> OTHER INFORMATION: c is dideoxycytidine

<400> SEQUENCE: 30
tttttactnn nnnnnnnnnn nnnnnnnnng tcgtcaagat gctaccgttc aggc    54

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
cctgaacggt agcatcttga cgac    24

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quncher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 32
aaaaaaaaac gcggcccgg                                                19

<210> SEQ ID NO 33
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 33
ccgggccgcg ttttttttta gtcgtcaaga tgctaccgtt cagg                    44

<210> SEQ ID NO 34
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: linked to a fluorophore at the 3' end

<400> SEQUENCE: 34
cctgaacggt agcatcttga cgactaaaaa aaaacgcggc ccgg                    44

<210> SEQ ID NO 35
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 35
ccgggccgcg ttttttttta gtcgtcaaga tgctaccgtt cagg                    44

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
cctgaacggt agcatcttga cgac                                          24

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 37
aaaaaaaaac gcggcccgg                                                19

<210> SEQ ID NO 38
<211> LENGTH: 44
<212> TYPE: DNA

```
<213> ORGANISM: Artificial Sequence
<220> FEATURE:
<223> OTHER INFORMATION: Synthetic oligonucleotide

<400> SEQUENCE: 38
ccgggccgcg ttttttttta gtcgtcaaga tgctaccgtt cagg          44

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 39
cctgaacggt agcatcttga cgac                                24

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 40
aaaaaaaaac gcggcccgg                                      19

<210> SEQ ID NO 41
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 41
ccgggccgcg ttttttttta cgtcgtcaag atgctaccgt tcagg         45

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 42
cctgaacggt agcatcttga cgac                                24

<210> SEQ ID NO 43
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end
```

<400> SEQUENCE: 43
aaaaaaaaac gcggcccgg                                                      19

<210> SEQ ID NO 44
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 44
ccgggccgcg ttttttttc aggtcgtcaa gatgctaccg ttcagg                          46

<210> SEQ ID NO 45
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: linked to a fluorophore at the 3' end

<400> SEQUENCE: 45
cctgaacggt agcatcttga cgactaaaaa aaaacgcggc ccgg                           44

<210> SEQ ID NO 46
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 46
ccgggccgcg tttttttta gtcgtcaaga tgctaccgtt cagg                            44

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 47
cctgaacggt agcatcttga cgac                                                 24

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 48
aaaaaaaaac gcggcccgg                                                      19

<210> SEQ ID NO 49

```
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 49
ccgggccgcg ttttttttta cgtcgtcaag atgctaccgt tcagg            45

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
cctgaacggt agcatcttga cgac                                   24

<210> SEQ ID NO 51
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 51
aaaaaaaaac gcggcccgg                                         19

<210> SEQ ID NO 52
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 52
ccgggccgcg tttttttttc aggtcgtcaa gatgctaccg ttcagg           46

<210> SEQ ID NO 53
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 53
cctgaacggt agcatcttga cgactaaaaa aaaacgcggc ccgg             44

<210> SEQ ID NO 54
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 54
ccgggccgcg ttttttttta gtcgtcaaga tgctaccgtt cagg             44
```

-continued

```
<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
cctgaacggt agcatcttga cgacg                                          25

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: linked to a fluorophore at the 3' end

<400> SEQUENCE: 56
aaaaaaaaac gcggcccgg                                                 19

<210> SEQ ID NO 57
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 57
ccgggccgcg ttttttttta cgtcgtcaag atgctaccgt tcagg                    45

<210> SEQ ID NO 58
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 58
cctgaacggt agcatcttga cgacc                                          25

<210> SEQ ID NO 59
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 59
aaaaaaaaac gcggcccgg                                                 19

<210> SEQ ID NO 60
<211> LENGTH: 46
<212> TYPE: DNA
<213> ORGANISM: Artificial Sequence
<220> FEATURE:
<223> OTHER INFORMATION: Synthetic oligonucleotide
```

```
<400> SEQUENCE: 60
ccgggccgcg ttttttttc aggtcgtcaa gatgctaccg ttcagg         46

<210> SEQ ID NO 61
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 61
cctgaacggt agcatcttga cgactaaaaa aaaacgcggc cgg            44

<210> SEQ ID NO 62
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 62
ccgggccgcg ttttttttta gtcgtcaaga tgctaccgtt cagg           44

<210> SEQ ID NO 63
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (63)..(63)
<223> OTHER INFORMATION: linked to a fluorophore at the 3' end

<400> SEQUENCE: 63
cctgaacggt agcatcttga cgacgtaaaa aaaaacgcgg cccgg          45

<210> SEQ ID NO 64
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 64
ccgggccgcg tttttttta cgtcgtcaag atgctaccgt tcagg           45

<210> SEQ ID NO 65
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 65
cctgaacggt agcatcttga cgacct                              26

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
```

```
<220> FEATURE:
<221> NAME/KEY: misc_feature
<222> LOCATION: (19)..(19)
<223> OTHER INFORMATION: linked to a fluorophore at the 3' end

<400> SEQUENCE: 66
aaaaaaaaac gcggcccgg                                                        19

<210> SEQ ID NO 67
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 67
ccgggccgcg ttttttttc aggtcgtcaa gatgctaccg ttcagg                           46

<210> SEQ ID NO 68
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 68
atagagcgag ccagtgctag ggtgagtggc caag                                       34

<210> SEQ ID NO 69
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 69
atagagcgag ccagtgctag ggtgagtggc caag                                       34

<210> SEQ ID NO 70
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 70
gcactggctc gctcta                                                           16

<210> SEQ ID NO 71
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 71
```
atagagcgag ccagtgctag ggtgagtggc caag                                    34

<210> SEQ ID NO 72
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: linked to Cy5 at the 3' end

<400> SEQUENCE: 72
gcactggctc gctctan                                                       17

<210> SEQ ID NO 73
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 73
atagagcgag ccagtgctag ggtgagtggc caag                                    34

<210> SEQ ID NO 74
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 74 gcactggc                                                                  8

<210> SEQ ID NO 75
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(35)
<223> OTHER INFORMATION: linked to an antibody at the 3' end

<400> SEQUENCE: 75
catagagcga gccagtgcta gggtgagtgg ccaag                                   35

<210> SEQ ID NO 76
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: linked to Cy5 at the 3' end

<400> SEQUENCE: 76
gcactggctc gctctan                                                       17

```
<210> SEQ ID NO 77
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(35)
<223> OTHER INFORMATION: linked to an antibody at the 3' end

<400> SEQUENCE: 77
caatgtccag gccagtgcta gggtgagtgg ccaag                              35

<210> SEQ ID NO 78
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 78
gcactggctc gctcta                                                   16

<210> SEQ ID NO 79
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(35)
<223> OTHER INFORMATION: linked to an antibody at the 3' end

<400> SEQUENCE: 79
caagtcagtg accagtgcta gggtgagtgg ccaag                              35

<210> SEQ ID NO 80
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 80
gcactggctc gctcta                                                   16

<210> SEQ ID NO 81
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to Cy5 at the 5' end
<220> FEATURE:
<221> NAME/KEY: misc_feature
<222> LOCATION: (18)..(35)
<223> OTHER INFORMATION: n is a, c, g, or t

<400> SEQUENCE: 81
acgtacgctc gtgccgcnnn nnnnnnnnn nnnnn                               35

<210> SEQ ID NO 82
<211> LENGTH: 17
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: linked to Cy3 at the 3' end

<400> SEQUENCE: 82
gcggcacgag cgtacgn                                                  17

<210> SEQ ID NO 83
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to Cy5 at the 5' end
<220> FEATURE:
<221> NAME/KEY: misc_feature
<222> LOCATION: (18)..(35)
<223> OTHER INFORMATION: n is a, c, g, or t

<400> SEQUENCE: 83
acctgcgctc gtgccgcnnn nnnnnnnnn nnnnn                               35

<210> SEQ ID NO 84
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 84
gcggcacgag cgtacg                                                   16

<210> SEQ ID NO 85
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to Cy5 at the 5' end
<220> FEATURE:
<221> NAME/KEY: misc_feature
<222> LOCATION: (18)..(35)
<223> OTHER INFORMATION: n is a, c, g, or t

<400> SEQUENCE: 85
agcatcgctc gtgccgcnnn nnnnnnnnn nnnnn                               35

<210> SEQ ID NO 86
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 86
gcggcacgag cgtacg                                                   16

<210> SEQ ID NO 87
<211> LENGTH: 50
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 87
gaaccggtga gtgggatagc gctacgcctg aacggtagca tcttgacgac          50

<210> SEQ ID NO 88
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: c is dideoxycytidine

<400> SEQUENCE: 88
tttttagtcg tcaagatgct accgttcagg c                               31

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
cctgaacggt agcatcttga cgac                                       24

<210> SEQ ID NO 90
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: c is dideoxycytidine

<400> SEQUENCE: 90
tttttagtcg tcaagatgct accgttcagg c                               31

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
cctgaacggt agcatcttga cgac                                       24

<210> SEQ ID NO 92
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (32)..(32)
```

```
<223> OTHER INFORMATION: c is dideoxycytidine

<400> SEQUENCE: 92
tttttatgtc gtcaagatgc taccgttcag gc                                          32
```

ON-SLIDE STRAINING BY PRIMER EXTENSION

STATEMENT REGARDING FEDERALLY SPONSORED RESEARCH

This invention was made with Government support under contract W81XWH-12-1-0591 awarded by the Department of Defense and under contracts GM104148 and HHSN268201000034C awarded by the National Institutes of Health. The Government has certain rights in the invention.

BACKGROUND

Several major approaches have been used so far for single-cell antigen cytometry. Among the most popular are single cell PCR, fluorescence activated flow cytometry, mass cytometry and single cell sequencing. These (fluorescence and mass-based cytometry) approaches are limited from either inability to breach the multiplexing levels of more than 100 parameters per analyte (cell in this case) or from inability to achieve high throughput (single cell sequencing). Also these methods are not appropriate or readily modified to enable cell multiplexed analysis of archived tissues and slide based samples.

Disclosed herein are several related methods for capture agent detection that are based on labeling the capture agent with DNA and subsequent detection of this DNA by primer extension.

SUMMARY

Provided herein is a method for analyzing a planar sample. In certain embodiments, the method comprises: (a) incubating the planar sample (e.g., a tissue section such as a formalin-fixed, paraffin-embedded (FFPE) section) with a capture agent under conditions by which the capture agent specifically binds to complementary sites in the planar sample, wherein: (i) the capture agent is linked to a double-stranded oligonucleotide that comprises a first strand and a second strand; (ii) the capture agent is linked to a double-stranded oligonucleotide by the 5' end of the first strand; and (iii) the 3' end of the first strand is recessed relative to the 5' end of the second strand, thereby producing an 5'-overhang; (b) crosslinking the capture agent to planar sample; (c) contacting the planar sample with a polymerase and a nucleotide mix, thereby adding one or more nucleotides to the overhang; and (d) reading a fluorescent signal generated by addition of the one or more nucleotides to the overhang using fluorescence microscopy, thereby producing an image showing the pattern of binding of the capture agent to the planar sample.

In certain embodiments, the method includes contacting the planar sample with a polymerase and a nucleotide mix that comprises a fluorescent nucleotide, thereby adding the fluorescent nucleotide to the overhang; and reading a fluorescent signal generated by addition of the fluorescent nucleotide to the overhang. In these embodiments, the fluorescent signal that is read may be, for example, emitted directly from the added nucleotide or may be a FRET signal generated by energy transfer, e.g., between two fluorescent nucleotides that are added to the overhang or between a first fluorescent nucleotide added to overhang and a second fluorescent nucleotide that is present in the second strand.

In alternative embodiments, extension of the first strand may remove a quencher from a quenched fluorescently labeled oligonucleotide that is hybridized to the second strand, downstream from the first strand.

Also provided herein is an capture agent that is linked to a double-stranded oligonucleotide, wherein: (i) the double-stranded oligonucleotide comprises a first strand and a second strand; (ii) the capture agent is linked to the 5' end of the first strand; and (iii) the 3' end of the first strand is recessed relative to the 5' end of the second strand, thereby producing an 5'-overhang.

Also provided herein is an capture agent composition comprising a plurality of capture agents that recognize different complementary sites. In these embodiments, each of the capture agents is linked to a double-stranded oligonucleotide that comprises a first strand and a second strand; the capture agents are linked to a double-stranded oligonucleotide by the 5' end of first strand; the 3' end of the first strand in each of the double-stranded oligonucleotides is recessed relative to the 5' end of the second strand, thereby producing an 5'-overhang; and the overhang is different for each of the capture agents. In some cases, the sequence of the first strand is the same for each of the capture agents; and the sequence of the second strand is different for each of the capture agents.

While DNA sequences are routinely set forth in 5' to 3' direction, for the ease description, certain DNA sequences in the text below are described in the 3' to 5'-direction. In each such case the directionalty is specifically annotated.

In embodiments that use a reversible terminator ("reversible terminator" approach), the overhangs may be of the formula 3'-$N_{4n}N_1/N_2/N_3$-5'-optionally followed by short stretch (e.g., 1-5 residues) of random nucleotides on the 5' end to increase the overall polymerase residence on the DNA duplex, where $N_1$, $N_2$, $N_3$ and $N_4$ are different nucleotides selected from G, A, T and C and n is 0, 1 or more (i.e., population contains single nucleotide overhangs of nucleotides $N_1$, $N_2$ and $N_3$ or the population of overhangs comprises two nucleotide overhangs of sequence 3'-$N_4N_1$-5',3'-$N_4N_2$-5' and 3'-$N_4N_3$-5'-5' and, optionally overhangs of sequence, 3'-$N_4N_4N_1$-5',3'-$N_4N_4N_2$-5' and 3'-$N_4N_4N_3$-5' and so on (e.g., four nucleotide overhangs of sequence 3'-$N_4N_4N_4N_1$-5',3'-$N_4N_4N_4N_2$-5' and 3'-$N_4N_4N_4N_3$-5').

In these embodiments, the overhangs may be of a more general formula 3'-$XN_1/N_2/N_3$-5', where $N_1$, $N_2$, $N_3$ are different nucleotides selected from G, A, T and C and X is a nucleotide stretch of bases Xi (such that Xi are different nucleotides selected from G, A, T and C) of random composition and length (i.e., the population of overhangs comprises two nucleotide overhangs of sequence 3'-$X_1N_1$-5',3'-$X_1N_2$-5' and 3'-$X_1N_3$-5' and, optionally overhangs of sequence, 3'-$N_1X_1X_2$-5',3'-$N_2X_1X_2$-5' and 3'-$N_3X_1X_2$-5' and so on (e.g., four nucleotide overhangs of sequence 3'-$N_1X_1X_2X_3$-5',3'-$N_2X_1X_2X_3$-5' and 3'-$N_3X_1X_2X_3$-5'). In many embodiments, this population additionally contains single nucleotide overhangs of nucleotides $N_1$, $N_2$ and $N_3$.

In embodiments that rely on a "missing base" approach, the overhangs may be of the formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C. For example, the population of overhangs comprises 5' overhangs of sequence 3'-$N_1$-5' and 3'-$N_2$-5' or optionally 3'-$N_3N_1$-5' and 3'-$N_3N_2$-5' or 3'-$N_3N_4N_1$-5' and 3'-$N_3N_4N_2$-5' and, optionally, overhangs of sequence 3'-$N_3N_4N_3N_1$-5' and 3'-$N_3N_4N_3N_2$-5' and so on (e.g., overhangs of sequence 3'-$N_3N_4N_3N_4N_1$-5' and 3'-$N_3N_4N_3N_4N_2$-5' and then 3'-$N_3N_4N_3N_4N_3N_1$-5' and 3'-$N_3N_4N_3N_4N_3N_2$-5').

In these embodiments the overhangs may also be of a more general formula 3'-$YN_1/N_2$-5', wherein Y is a nucleotide sequence of length n (n is 0, 1 or more) composed of alternating random length stretches of bases $N_3$ and $N_4$ such that the order number of $N_3$-stretches is odd and of $N_4$ stretches is even and wherein $N_1$, $N_2$, $N_3$ and $N_4$ are different nucleotides selected from G, A, T and C. For example, the population of overhangs comprises overhangs of sequence 3'-$N_1$-5' and 3'-$N_2$-5' or optionally 3'-$N_3N_3N_1$-5' and 3'-$N_3N_3N_2$-5' or 3'-$N_3N_3N_4N_1$-5' and 3'-$N_3N_3N_4N_2$-5' and, optionally, overhangs of sequence 3'-$N_3N_3N_3N_3N_4N_4N_3N_3N_3N_1$-5' and 3'-$N_3N_3N_3N_3N_4N_4N_3N_3N_3N$-5'$_2$ and so on).

Also provided is a method for analyzing a planar sample in a multiplex way. In certain embodiments, this method comprises: (a) incubating the planar sample with the above-summarized capture agent composition under conditions by which the capture agents specifically bind to complementary sites in the planar sample; (b) crosslinking the capture agent to planar sample; (c) contacting the planar sample with a polymerase and either an incomplete nucleotide mix of labeled and unlabeled bases or a nucleotide mix where some or all bases are fluorescent and some or all bases constitute reversible terminator nucleotides or fluorescent reversible terminator nucleotides; and (d) reading, using fluorescence microscopy, a fluorescent signal generated by addition of a fluorescent nucleotide to some but not all of the capture agents.

In certain embodiments, the method comprises: (c) contacting the planar sample with a polymerase and: (i) a nucleotide mix that comprises fluorescent nucleotides that are complementary to $N_1$, $N_2$ and $N_3$ and a reversible terminator nucleotide that is complementary to $N_4$ or (ii) a nucleotide mix that comprises fluorescent reversible terminator nucleotides that are complementary to $N_1$, $N_2$ and $N_3$ and a reversible terminator nucleotide that is complementary to $N_4$ or (iii) a nucleotide mix that comprises fluorescent nucleotides that are complementary to $N_1$, and $N_2$, an unlabeled nucleotide that is complementary to $N_3$, and no nucleotide that is complementary to $N_4$, thereby adding fluorescent nucleotides onto the double-stranded oligonucleotides of some but not all of the capture agents; and (d) reading, using fluorescence microscopy a fluorescent signal generated by addition of a fluorescent nucleotide to some but not all of the capture agents.

In certain embodiments, the overhangs may be of the formula 3'-$N_{4n}N_1/N_2/N_3$-5' optionally followed by short stretch (e.g., 1-5 residues) of random nucleotides on the 5' end to increase the overall polymerase residence on the DNA duplex, or 3'-$XN_1/N_2/N_3$-5', where $N_1$, $N_2$, $N_3$ are different nucleotides selected from G, A, T and C and n is 1 or more and X is a nucleotide stretch of bases Xi (such that Xi are different nucleotides selected from G, A, T and C) of random composition and length; and step (c) comprises contacting the planar sample with a polymerase and a nucleotide mix that comprises fluorescent nucleotides (being reversible terminators or not) that are complementary to $N_1$, $N_2$ and $N_3$ and an unlabeled reversible terminator nucleotide that is complementary to $N_4$. These embodiments may further comprise (e) inactivating the fluorescent signal, simultaneously deprotecting the reversible terminator nucleotide (f) blocking the planar sample; and (g) repeating steps (c), (d), (e) and (f). In some embodiments, step (g) may comprise repeating steps (c), (d), (e) and (f) multiple times.

Alternatively, in some embodiments, the overhangs may be of the formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C, and step (c) comprises contacting the planar sample with a polymerase and a nucleotide mix that comprises fluorescent nucleotides that are complementary to $N_1$, and $N_2$, an unlabeled nucleotide that is complementary to $N_3$ and no nucleotide that is complementary to $N_4$. These embodiments may further comprise (e) inactivating the fluorescent signal, (f) blocking the planar sample and (g) contacting the planar sample with a polymerase and an unlabeled nucleotide that is complementary to $N_4$; and (h) repeating steps (c), (d), (e) and (f). In some cases, step (g) may comprise repeating steps (c), (d), (e) and (f) multiple times.

In alternative embodiments, the double-stranded oligonucleotides may each comprise a fluorescently labeled oligonucleotide hybridized to the second strand downstream from first strand, wherein the fluorescently labeled oligonucleotide comprises a quencher and extension of the first strand removes the quencher from some but not all of the quenched fluorescently labeled oligonucleotides, thereby generating a fluorescent signal for some but not all of the capture agents.

In other embodiments, the capture agent is linked to a single stranded oligonucleotide, which can be either unlabeled or labeled with FRET acceptor fluorophore. Such a single stranded nucleotide incorporates a dedicated sequence that hybridizes to a complementary oligonucleotide which is to be extended with unlabeled base or with a base labeled with a FRET excitation fluorophore, thereby generating a fluorescent signal for some but not all of the capture agents.

BRIEF DESCRIPTION OF THE FIGURES

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The drawings are not intended to limit the scope of the present teachings in any way.

FIG. 5A-5D schematically illustrates an exemplary design of oligonucleotide duplexes for "reversible terminator" and "missing base" multiplexing methods. SEQ ID NOS: 5-12.

FIG. 8 schematically illustrates a multiplexed detection method that relies on removing quenchers from labeled oligonucleotides. Step 1: SEQ ID NOS 36-44, Step 2: SEQ ID NOS: 45-52, Step 3: SEQ ID NOS: 53-60, Step 4: SEQ ID NOS: 61-67.

FIGS. 9A and 9B schematically illustrate an embodiment that relies on cyclical re-annealing of polymerase priming nucleotides and a variant of the same approach that utilizes FRET. SEQ ID NOS: 68-80.

FIG. 10 schematically illustrate an embodiment that relies on cyclical re-annealing of polymerase priming nucleotides and a variant of the same approach that utilizes FRET. SEQ ID NOS: 81-86.

DEFINITIONS

Figures 1A, 1B:
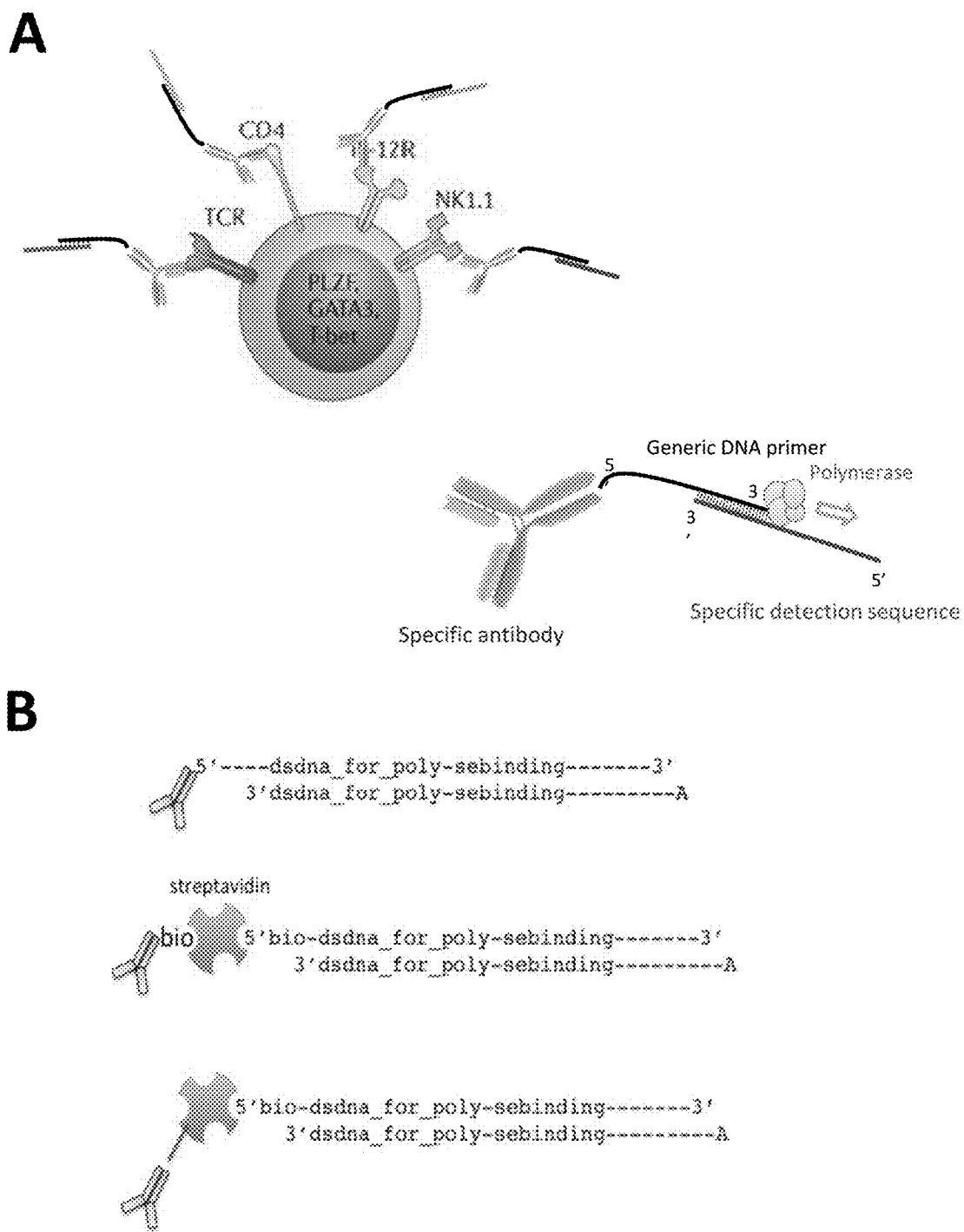
FIG. 1A-1B (A) schematically illustrates a detection reagent composed of a combination of a capture agent that is conjugated to a double-stranded oligonucleotide. Upon detection and removal of unbound detection reagent the binding pattern is rendered by polymerase driven primer extension. Panel (B) schematically illustrates three approaches for linking the capture agent (an antibody in this case, but not excluding other possible capture agents) to a double stranded oligonucleotide (i.e., by chemical conjugation of the upper strand oligonucleotide to the capture agent; using streptavidin as an intermediate to connect biotinylated antibody and biotinylated oligonucleotide; and by linking biotinylated oligonucleotide to antibody chemically conjugated to streptavidin).

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "biological feature of interest" refers to any part of a cell that can be indicated by binding to a capture agent. Exemplary biological features of interest include cell walls, nuclei, cytoplasm, membrane, keratin, muscle fibers, collagen, bone, proteins, nucleic acid (e.g., mRNA or genomic DNA, etc). fat, etc. A biological feature of interest can also be indicated by immunohistological methods, e.g., a capture agent that is linked to an oligonucleotide. In these embodiments, the capture agent binds to an site, e.g., a protein epitope, in the sample. Exemplary epitopes include, but are not limited to carcinoembryonic antigen (for identification of adenocarcinomas, cytokeratins (for identification of carcinomas but may also be expressed in some sarcomas) CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas), CD3 (for identification of T-cell lymphomas). Complementary nucleic acid molecules (e.g., DNA and/or RNA) in the sample provide binding complementary sites for oligonucleotide probes.

As used herein, the term "multiplexing" refers to using more than one label for the simultaneous or sequential detection and measurement of biologically active material.

As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, minibodies, single-chain antibodies, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e. g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding reagent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

A "plurality" contains at least 2 members. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

As used herein, the term "labeling" refers to attaching a detectable fluorophore to specific sites in a sample (e.g., sites containing an epitope for the antibody being used, for example) such that the presence and/or abundance of the sites can be determined by evaluating the presence and/or abundance of the label.

As used herein, the term "planar sample" refers to a substantially planar, i.e., two dimensional, material that contains cells. A planar cellular sample can be made by, e.g., growing cells on a planar surface, depositing cells on a planar surface, e.g., by centrifugation, or by cutting a three dimensional object that contains cells into sections and mounting the sections onto a planar surface, i.e., producing a tissue section. The cells may be fixed using any number of reagents including formalin, methanol, paraformaldehyde, methanol:acetic acid etc.

As used herein, the term "tissue section" refers to a piece of tissue that has been obtained from a subject, fixed, sectioned, and mounted on a planar surface, e.g., a microscope slide.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a microscope slide.

As used herein, the term "spatially-addressable measurements" refers to a set of values that are each associated with a specific position on a surface. Spatially-addressable measurements can be mapped to a position in a sample and can be used to reconstruct an image of the sample.

A "diagnostic marker" is a specific biochemical in the body which has a particular molecular feature that makes it useful for detecting a disease, measuring the progress of disease or the effects of treatment, or for measuring a process of interest.

A "pathoindicative" cell is a cell which, when present in a tissue, indicates that the animal in which the tissue is located (or from which the tissue was obtained) is afflicted with a disease or disorder. By way of example, the presence of one or more breast cells in a lung tissue of an animal is an indication that the animal is afflicted with metastatic breast cancer.

The term "complementary site" is used to refer to an epitope for an antibody or aptamer, or a nucleic acid molecule if the capture agent is an oligonucleotide probe. Specifically, if the capture agent is an antibody, then the complementary site for the capture agent is the epitope in the sample to which the antibody binds. If the capture agent is an oligonucleotide probe, then the complementary site for the capture agent is a complementary sequence in a DNA or RNA molecule in the sample.

The term "epitope" as used herein is defined as small chemical groups on the antigen molecule that is bound to by an antibody. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

As used herein, the term "incubating" refers to maintaining a planar sample and capture agent under conditions (which conditions include a period of time, a temperature, an appropriate binding buffer and a wash) that are suitable for specific binding of the capture agent to molecules (e.g., epitopes or complementary nucleic acid) in the planar sample.

As used herein, the term "capture agent" refers to an agent that can specifically bind to complementary sites in a planar sample. Exemplary capture agents include, e.g., an antibody, an aptamer, and an oligonucleotide probe (which may be DNA or RNA) that hybridizes to a binding site.

As used herein, the term "capture agent that is linked to a double stranded oligonucleotide" refers to a capture agent, e.g., an antibody or an oligonucleotide probe, that is non-covalently (e.g., via a streptavidin/biotin interaction) or covalently (e.g., via a click reaction or the like) linked to an oligonucleotide (which may be composed of two single-stranded oligonucleotide strands that are hybridized together) in a way that the capture agent can still bind to its binding site and the 3' end of one of the oligonucleotides is accessible to a polymerase. The oligonucleotide and the capture agent may be linked via a number of different methods, including those that use maleimide or halogen-containing group, which are cysteine-reactive.

As used herein, the term "oligonucleotide" refers to a multimer of at least 10, e.g., at least 15 or at least 30 nucleotides. In some embodiments, an oligonucleotide may be in the range of 15-200 nucleotides in length.

As used herein, the term "reading" in the context of reading a fluorescent signal, refers to obtaining an image by scanning or by microscopy, where the image shows the pattern of fluorescence as well as the intensity of fluorescence in a field of view.

As used herein, the term "primer" is an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. A primer may be at least 10, e.g., at least 15 or at least 30 nucleotides in length.

As used herein, the term "single nucleotide 5' overhang" refers to a 5' overhang, where the overhang is a single nucleotide in length. Likewise, a "two nucleotide 5' overhang" is a 5' overhang, where the overhang is two nucleotides in length. The 3' end is recessed in a 5' overhang.

In certain cases, the various nucleotides of an overhang may be referred to by their position, e.g., "first position" and "second position". In these cases, the "position" is relative to the recessed 3' end. As such, in a multiple base 5' overhang, the "first" position of the overhang is immediately adjacent to the recessed 3' end and the "second" position of the overhang is immediately adjacent to the first position.

In certain cases, the complementary strands of a double stranded oligonucleotide may be referred to herein as being the "first" and "second" or the "top" and "bottom" strands. The assignment of a strand as being a "top" or "bottom" strand is arbitrary and does not imply any particular orientation, function or structure.

As used herein, the term "signal generated by", in the context of reading a fluorescent signal generated by addition of the fluorescent nucleotide, refers to a signal that is emitted directly from the fluorescent nucleotide, a signal that is emitted indirectly via energy transfer to another fluorescent nucleotide (i.e., by FRET).

As used herein, the term "fluorescently labeled oligonucleotide comprising a quencher" refers to an oligonucleotide that contains a fluorophore and a quencher, wherein the quencher quenches the fluorophore in the same oligonucleotide.

As used herein, the term "different" in the context of different 5' overhangs that are different, refers to overhangs that have a different sequence. Overhangs of different lengths (e.g., GATC vs GAT) implicitly have a different sequence, even through one sequence may be encompassed by the other.

As used herein, the term "adding to an overhang", in the context of adding one or more nucleotides to an overhang, refers to adding nucleotides to the recessed 3' end of a 5' overhang using the overhang as a template.

As used herein, the term "overhangs of the formula $3'-N_{4n}N_1/N_2/N_3-5'$ followed by an optional short stretch (e.g., 1-5 residues) of random nucleotides on the 5' end to increase the overall polymerase residence on the DNA duplex, where $N_1$, $N_2$, $N_3$ and $N_4$ are different nucleotides selected from G, A, T and C and n is 0, 1 or more", refers to a population of overhangs that contains single nucleotide overhangs of nucleotides $N_1$, $N_2$ and $N_3$ or the population of overhangs comprises two nucleotide overhangs of sequence $3'-N_4N_1-5'$, $3'-N_4N_2-5'$ and $3'-N_4N_3-5'-5'$ and, optionally overhangs of sequence, $3'-N_4N_4N_1-5'$, $3'-N_4N_4N_2-5'$ and $3'-N_4N_4N_3-5'$ and so on (e.g., four nucleotide overhangs of sequence $3'-N_4N_4N_4N_1-5'$, $3'-N_4N_4N_4N_2-5'$ and $3'-N_4N_4N_4N_3-5'$).

As used herein, the term "overhangs of the formula $3'-YN_1/N_2-5'$, optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C" refers to a population of overhangs of sequence $3'-N_1-5'$ and $3'-N_2-5'$ or optionally $3'-N_3N_1-5'$ and $3'-N_3N_2-5'$ or $3'-N_3N_4N_1-5'$ and $3'-N_3N_4N_2-5'$ and, optionally, overhangs of sequence $3'-N_3N_4N_3N_1-5'$ and $3'-N_3N_4N_3N_2-5'$ and so on (e.g., overhangs of sequence $3'-N_3N_4N_3N_4N_1-5'$ and $3'-N_3N_4N_3N_4N_2-5'$ and then $3'-N_3N_4N_3N_4N_3N_1-5'$ and $3'-N_3N_4N_3N_4N_3N_2-5'$).

As used herein, the term "alternating stretches" refers to two nucleotides stretches, where one "stretch" is a contiguous sequence of, e.g., up to 10, of the same nucleotide (e.g., a G, A, T or C), and the second stretch is contiguous sequence of, e.g., up to 10, of a different nucleotide, that alternate with one another, i.e., one stretch (e.g., a string of T's) occupies the odd positions and the other stretch (e.g., a string of A's) occupies the even positions.

As used herein, the term "incomplete nucleotide mix" comprises a nucleotide mix that contains one, two or three nucleotides (but not all four nucleotides) selected from G, A, T and C. The nucleotides may be labeled or unlabeled.

As used herein, the term "reversible terminator" refers to a chemically modified nucleotide base that when incorporated into growing DNA strand by DNA polymerase blocks further incorporation of bases. Such "reversible terminator" base and DNA strand can be deprotected by chemical treatment and following such deprotection DNA strand can be further extended by DNA polymerase.

As used herein, the term "fluorescently labeled reversible terminator" refers to a "reversible terminator" base which is labeled by fluorophore through linker cleavable by same treatment which is used to deprotect the DNA strand which ends with this base. Deprotecting the "fluorescently labeled reversible terminator" simultaneously activates the DNA strand for further extension and removes the fluorescent label from it.

For ease of description, many of the sequences described herein are written out in the 3' to 5' direction.

Other definitions of terms may appear throughout the specification.

DETAILED DESCRIPTION

In some embodiments the method comprises labeling a planar sample (e.g., an FFPE section mounted on a planar surface such as a microscope slide) with a capture agent that specifically binds to complementary sites in the planar sample. This step is done under conditions by which the capture agent binds to complementary sites in the planar sample, methods for which are well known. In these embodiments, the capture agent is linked to a double-stranded oligonucleotide that comprises a first strand and a second strand (e.g., two oligonucleotide that are hybridized together) and the capture agent is linked (covalently or non-covalently via a biotin) to the double-stranded oligonucleotide by the 5' end of the first strand, and the 3' end of the first strand is recessed relative to the 5' end of the second strand, thereby defining an overhang. After the capture agent has bound to the planar sample, the capture agent is cross-linked the planar sample. This crosslinking step may be done using any amine-to-amine crosslinker (e.g. formaldehyde, disuccinimiyllutarate or another reagents of similar action) although a variety of other chemistries can be used to cross-link the capture agent to the planar sample if desired. The method comprises reading a fluorescent signal generated by addition of a nucleotide in the overhang. This step may be done by contacting the planar sample with a polymerase and a nucleotide mix, thereby adding one or more nucleotides to the overhang; and reading a fluorescent signal generated by addition of the one or more nucleotides to the overhang.

As will be described in greater detail below, the fluorescent signal may be generated by a variety of different methods. For example, in some embodiments, the flouorescent signal may be fluorescence from a fluorescent nucleotide added to the end of the primer, or a FRET (fluorescence resonance energy transfer) signal resulting from the same. In other embodiments, the signal may generated by removing a quencher from a fluorescently labeled oligonucleotide that is also hybridized to the oligonucleotide.

In any implementation of the method, the reading step may be followed by inactivating the fluorescence after reading so that other binding events can be detected and read. In these embodiments, the fluorescence may be inactivated by peroxide-based bleaching, cleavage of fluorophore linked to nucleotide through cleavable linker (e.g. using TCEP as a cleaving reagent), base-exchange by exo+ polymerase such as Vent, or subsequent incorporation of quencher, for example.

Also, as will be described in greater detailed below, the method may be multiplexed in a way that a single planar sample can be interrogated by a plurality of different capture agents, where each antibody is linked to different oligonucleotides (i.e., oligonucleotides of different sequence). In multiplex embodiments, the planar sample may be labeled using at least 5, at least 10, at least 20, at least 30, at least 50, or at least 100, up to 150 or more capture agents that are each linked to a different oligonucleotide, and binding of the capture agents can be separately read using a fluorescence microscope equipped with an appropriate filter for each fluorophore, or by using dual or triple band-pass filter sets to observe multiple fluorophores. See, e.g., U.S. Pat. No. 5,776,688.

Figure 2:
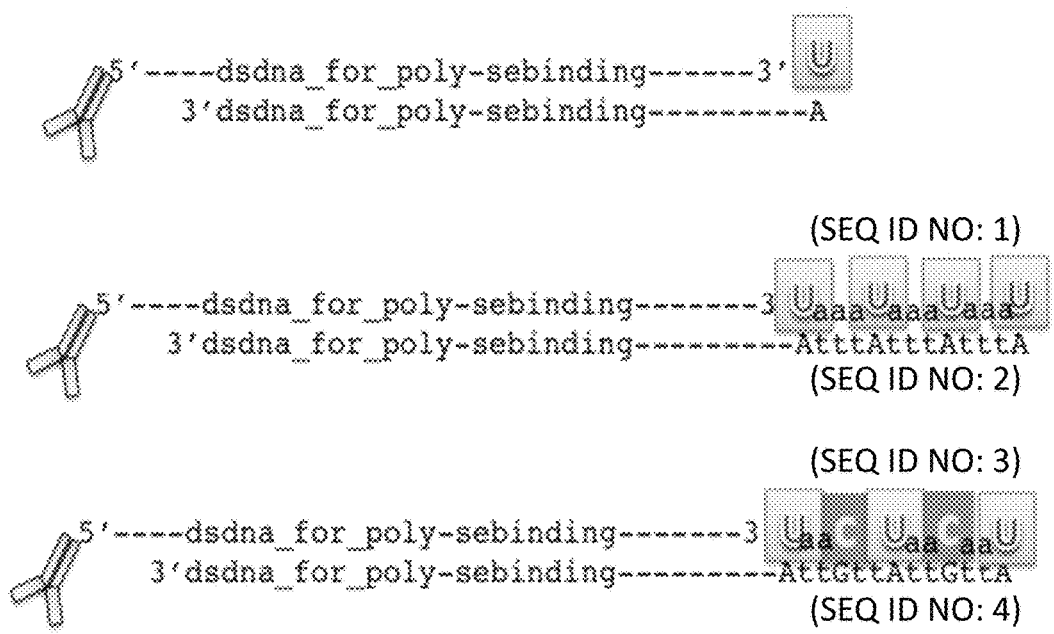
FIG. 2 schematically illustrates examples of capture agents that are bound to double-stranded oligonucleotides that have different overhangs. Such different overhangs represent a strategy to increase signal harvested from a particular capture agent by multiplication of positions in lower strand oligonucleotide complementary to detector base (dU in this case). The lower panel also shows how a different base labeled with a different fluorophore can be used as a FRET excitation pair for the "Detector" base. SEQ ID NOS: 1-4.

As summarized above, a capture agent used in the method may be linked to a double-stranded oligonucleotide that contains a 5' overhang (i.e., a recessed 3' end that can be extended by a polymerase). An example of such a capture agent is shown in FIGS. 1 and 2. In the example shown in FIG. 1B, the overhang is a single nucleotide overhang (e.g., an A), although a longer overhang (e.g., at least 2, at least 3, at least 4, at least 5, at least 6, at least 8, at least 10, at least 20, or at least at least 30, may be useful for other applications (e.g., multiplexed applications). As shown in FIG. 5 A-D, in certain cases, the overhang may contain a repeated sequence, e.g., 2, 3, 4, 5, or 6 or more repeats of the same sequence of 2, 3, 4, 5 or 6 nucleotides, thereby allowing the capture agent to be used in multiplexed applications as described below. In certain embodiments, the double stranded oligonucleotide may have a recessed 3' end at the other end of the oligonucleotide (i.e., at the end closest to the capture agent). However, this end is not extendible. In certain circumstances, the double-stranded oligonucleotide may contain one or more third oligonucleotides that are hybridized to the overhang. In these embodiments, there will be a gap of 1, 2, 3, 4 or 5 or more nucleotides between the second strand of the double-stranded oligonucleotide and the oligonucleotide that is hybridized to the overhang (see, e.g., FIGS. 7 and 8). In multiplex embodiments, the plurality of capture agents may be distinguished by the sequence of the overhang and not by the sequence of the first strand of the double stranded oligonucleotide. In these embodiments, the second strand of the double stranded oligonucleotides is different for each of the capture agents.

In certain cases, the fluorophore used may be a coumarin, a cyanine, a benzofuran, a quinoline, a quinazolinone, an indole, a benzazole, a borapolyazaindacene and or a xanthene including fluorescein, rhodamine and rhodol. In multiplexing embodiments, fluorophores may be chosen so that they are distinguishable, i.e., independently detectable, from one another, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same area of the section).

Specific fluorescent dyes of interest include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g., Cy3, Cy5 and Cy7 dyes; coumarins, e.g., umbelliferone; benzimide dyes, e.g. Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc.; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, Napthofluorescein, Texas Red, Cy3, and Cy5, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 and TOPRO3 (Molecular Probes, Eugene, Oreg.). Further suitable distinguishable detectable labels may be found in Kricka et al. (Ann Clin Biochem. 39:114-29, 2002), Ried et al. (Proc. Natl. Acad. Sci. 1992: 89: 1388-1392) and Tanke et al. (Eur. J. Hum. Genet. 1999 7:2-11) and others.

In order to further illustrate the present invention, the following specific examples are given with the understanding that they are being offered to illustrate the present invention and should not be construed in any way as limiting its scope.

Example 1

In this example, the fluorescent signal may be produced by a fluorescent nucleotide that is added to the 3' end of the primer. This method may comprise reading a signal from the added fluorescent nucleotide, or reading a FRET signal generated by energy transfer between two fluorescent nucleotides that are added to the primer.

The example shown in FIGS. 1 and 2 shows how an antibody can be linked to a oligonucleotide chemically, or via biotin/streptavidin interactions (FIG. 1B) and how a fluorescent signal can be generated by adding a fluorescent nucleotide to the end of the primer (FIG. 2). In this example, the antigen is stained by an antibody that is coupled to a DNA dimer with an overhanging 5' end (lower strand) and recessed 3' end (upper strand) either chemically (FIG. 1 top panel) or through streptavidin (FIG. 1 bottom and middle panels).

After binding the capture agent to the tissue sample, the pattern of binding of the capture agent may be determined using an on-slide end fill-in reaction by using a suitable polymerase (e.g., by exo⁻ Klenow, Bst, Taq, Klentaq, or an exo⁻ Klenow-Vent mixture) and fluorescently labeled nucleotide (FIG. 1 and FIG. 2 top panel).

If necessary, the signal-to-noise ratio can be increased by: a) multimerization of position complementary to labeling nucleotide (FIG. 2, middle panel); or b) by generating a FRET between two nucleotides are incorporated, whereby the emission wavelength of one of the nucleotides (FIG. 2, bottom panel C on the figure) serves as an excitation wavelength for another (FIG. 2, bottom panel U on the figure).

Fluorescence may be inactivated before addition of subsequent staining reagents by any convenient method including, but not limited to photobleaching, peroxide-based bleaching, inactivation by ozone, cleavage of fluorophore linked to nucleotide through cleavable linker (e.g. using TCEP as a cleaving reagent), base-exchange by exo+ polymerase such as Vent, subsequent incorporation of quencher.

In these embodiments, after fluorescence has been inactivated, the method can be repeated, i.e., the planar sample may be re-stained using a different antibody and fluorescence can be read.

Multiplexing

Figure 3:
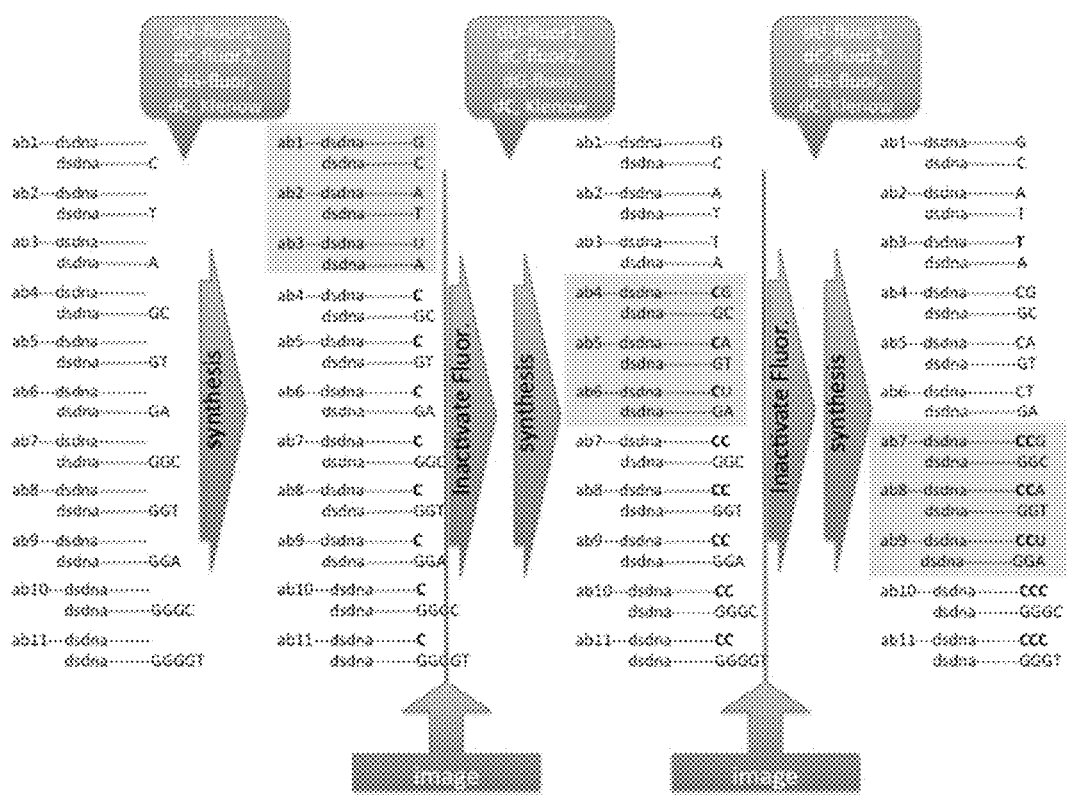
FIG. 3 schematically illustrates several cycles of a multiplexed detection method that relies on reversible dye terminators.
Figure 4:
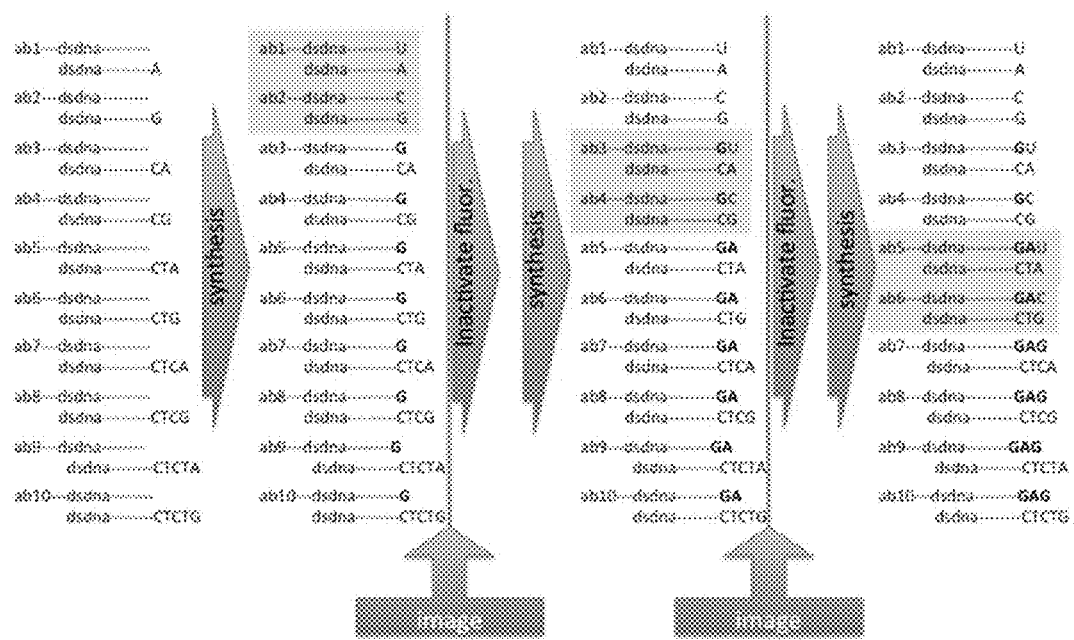
FIG. 4 schematically illustrates several cycles of a multiplexed detection method that relies on leaving out one of the four nucleotides per cycle.

Multiplexing can be implemented using specially designed oligonucleotides using two different approaches, referred to as the "reversible terminator" and "missing base" approaches, which are described in greater detail below. Both of these methods rely on a composition comprising a plurality of (e.g., at least 5, at least 10, at least 20, at least 30, at least 50, or at least 100, up to 150 or more) capture agents that recognize different complementary sites, wherein: each of the capture agents is linked to a double-stranded oligonucleotide that comprises a first strand and a second strand; the capture agents are linked to a double-stranded oligonucleotide by the 5' end of first strand; the 3' end of the first strand in each of the double-stranded oligonucleotides is recessed relative to the 5' end of the second strand, thereby producing an overhang; and the overhang is different for each of the capture agents. Examples of such compositions are illustrated in FIGS. 3 and 4. FIG. 3 shows a population of capture agents that have an overhang defined by the formula: 3'-$N_{4n}N_1/N_2/N_3$-5' followed by short stretch of random composition on the 5' end to increase the overall polymerase residence on the DNA duplex, where $N_1$, $N_2$, $N_3$ and $N_4$ are different nucleotides selected from G, A, T and C and n is 0, 1 or more. FIG. 4, on the other hand, shows a population of capture agents that have an overhang defined by the formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C. As illustrated in FIGS. 3, 4 and 5, the sequence of the first strand is the same for each of the capture agents; and the sequence of the second strand is different for each of the capture agents. In these embodiments, the different second strands make the overhangs different between the different capture agents.

In some embodiments, the multiplex methods generally comprise: (a) incubating a planar sample with an above-described antibody composition under conditions by which the capture agents bind to complementary sites in the planar sample; (b) cross-linking the capture agents to the planar sample; (c) contacting the planar sample with a polymerase and either an incomplete nucleotide mix of labeled and unlabeled bases or a nucleotide mix where some or all bases are fluorescent and some or all bases constitute reversible terminator nucleotides or fluorescent reversible terminator nucleotides; and (d) reading, using fluorescence microscopy, a fluorescent signal generated by addition a nucleotide to some but not all of the capture agents. Step (c) of this method may comprise (c) contacting the planar sample with a polymerase and:

(i) a nucleotide mix that comprises fluorescent nucleotides that are complementary to $N_1$, $N_2$ and $N_3$ and a reversible terminator nucleotide that is complementary to $N_4$ or (ii) a nucleotide mix that comprises fluorescent reversible terminator nucleotides that are complementary to $N_1$, $N_2$ and $N_3$ and a reversible terminator nucleotide that is complementary to $N_4$ or (iii) a nucleotide mix that comprises fluorescent nucleotides that are complementary to $N_1$, and $N_2$, an unlabeled nucleotide that is complementary to $N_3$, and no nucleotide that is complementary to $N_4$, thereby adding fluorescent nucleotides onto the double-stranded oligonucleotides of some but not all of the capture agents thereby adding fluorescent nucleotides onto the double-stranded oligonucleotides of some but not all of the capture agents; and (d) reading, using fluorescence microscopy, a fluorescent signal generated by addition of a fluorescent nucleotide to some but not all of the capture agents. Examples of such methods are described in greater detail below.

Figure 6:
FIG. 6 schematically illustrates an exemplary design of oligonucleotide duplexes for a strategy that allows one to reduce the length of the lower strand oligonucleotide, creating an overhang in the case of highly multiplexed capture agent panels. SEQ ID NOS: 13-30.

With reference to FIG. 6 it is expected that in the case when larger panels of capture agents are to be employed (e.g. 100 and more) the length of the read over the oligonucleotide overhangs may increase accordingly. This may or may not reduce the efficiency of staining due to accumulation of primer extension errors along the length of the oligonucleotide duplex. To circumvent such potential source of signal loss a slight modification of design can be implemented. The plurality of capture agents can be divided in sets such that number of capture agents in the set does exceed the capacity of the multiplexing protocol to render staining without significant signal loss (e.g. 30). Each such set of capture agents will be conjugated to "terminated" (the last 3' base is dideoxy- or propyl-modified) upper strand oligonucleotide of the same sequence as in the original version of the "missing base" approach. The lower strand oligos will incorporate an additional set-specific region which will serve as a landing spot for an additional primer which is to be on-slide hybridized to the particular subset of the total plurality of the antibodies at the time when they are to be rendered. This approach allows not to extend the reads beyond certain threshold and at the same time have an unlimited potential number of capture agents in the sample.

Reversible Terminator Method

This implementation of the method relies on reversible terminators, i.e., chain terminator nucleotides that can be de-protected after incorporation, thereby allowing further nucleotides to be added to that nucleotide.

This method can be implemented using a composition comprising a plurality of capture agents that are linked to double stranded oligonucleotides, as illustrated in FIG. 3. In these embodiments, the top strand of the double stranded oligonucleotide is linked to the capture agent and is same for each antibody, and the sequence of the bottom strand varies between capture agents. As shown on FIG. 5A, the 5' end of the lower strand of the double-stranded oligonucleotide (which forms the overhang) is of the general 3'-$N_{4n}N_1/N_2/N_3$-5' followed by short stretch of random nucleotides on the 5' end to increase the overall polymerase residence on the DNA duplex, where $N_1$, $N_2$, $N_3$ and $N_4$ are different nucleotides selected from G, A, T and C and n is 0, 1 or more. As shown on FIG. 5B a more general formula of lower oligonucleotide overhang 3'-$XN_1/N_2/N_3$-5', where $N_1$, $N_2$, $N_3$ are different nucleotides selected from G, A, T and C and X is a nucleotide stretch of bases Xi (such that Xi are different nucleotides selected from G, A, T and C) of random composition and length is also applicable in this method.

In certain embodiments, this method may comprise: (a) incubating a planar sample with a multiplex antibody composition in which the overhangs are of the formula 5'-$N_1/N_2/N_3N_{4n}$, wherein $N_1$, $N_2$, $N_3$ and $N_4$ are different nucleotides selected from G, A, T and C and n is 1 or more; under conditions by which the capture agents specifically bind to complementary sites in the planar sample; (b) cross-linking the capture agent to the planar sample; (c) contacting the planar sample with a polymerase and a nucleotide mix that comprises fluorescent nucleotides that are complementary to $N_1$, $N_2$ and $N_3$ and a reversible terminator nucleotide that is complementary to $N_4$; and (d) reading, using fluorescence microscopy, a fluorescent signal generated by addition of a nucleotide to some but not all of the capture agents. This cycle may be repeated by (e) inactivating the fluorescent signal, deprotecting the reversible terminator nucleotide and (f) blocking the planar sample; and repeating steps (c) and (d). In certain embodiments, the method may comprise repeating steps (c), (d) (e) and (f) multiple times. The reagent used for blocking may vary depending on the chemistry used. In certain embodiments, the sample may be blocked with a thiol-reactive compounds such as cysteine, glutathione or iodoacetamide.

For example, this method can be implemented using a composition comprising: a first antibody linked to a first double stranded oligonucleotide, wherein the first double stranded oligonucleotide comprises a single nucleotide 5' overhang comprising base $N_1$; a second antibody linked to a second double stranded oligonucleotide, wherein the second double stranded oligonucleotide comprises a single nucleotide 5' overhang comprising base $N_2$; a third antibody linked to a third double stranded oligonucleotide, wherein the third double stranded oligonucleotide comprises a single nucleotide 5' overhang comprising base $N_3$; a fourth antibody linked to a fourth double stranded oligonucleotide comprises a two nucleotide 5' overhang, wherein the first position of the overhang comprises base $N_4$ and the second position of the overhang is base $N_1$; a fifth antibody linked to a fifth double stranded oligonucleotide, wherein the fifth double stranded oligonucleotide comprises a two nucleotide 5' overhang, wherein the first position of the overhang comprises base $N_4$ and the second position of the overhang is base $N_2$; and a sixth antibody linked to a sixth double stranded oligonucleotide, wherein the sixth double stranded oligonucleotide comprises a two nucleotide 5' overhang, wherein the first position of the overhang comprises base $N_4$ and the second position of the overhang is base $N_3$, wherein $N_1$, $N_2$, $N_3$ and $N_4$ are different nucleotides selected from G, A, T and C. An example of such a population of capture agents is shown in FIG. 3.

In certain implementations, the composition may also contain a seventh antibody linked to a seventh double stranded oligonucleotide, wherein the seventh double stranded oligonucleotide comprises a multiple nucleotide 5' overhang, wherein the first position of the overhang comprises base $N_4$, the second position of the overhang is base $N_4$ and third is selected from $N_1$, $N_2$, and $N_3$.

Figures 13A, 13B, 13C, 13D:
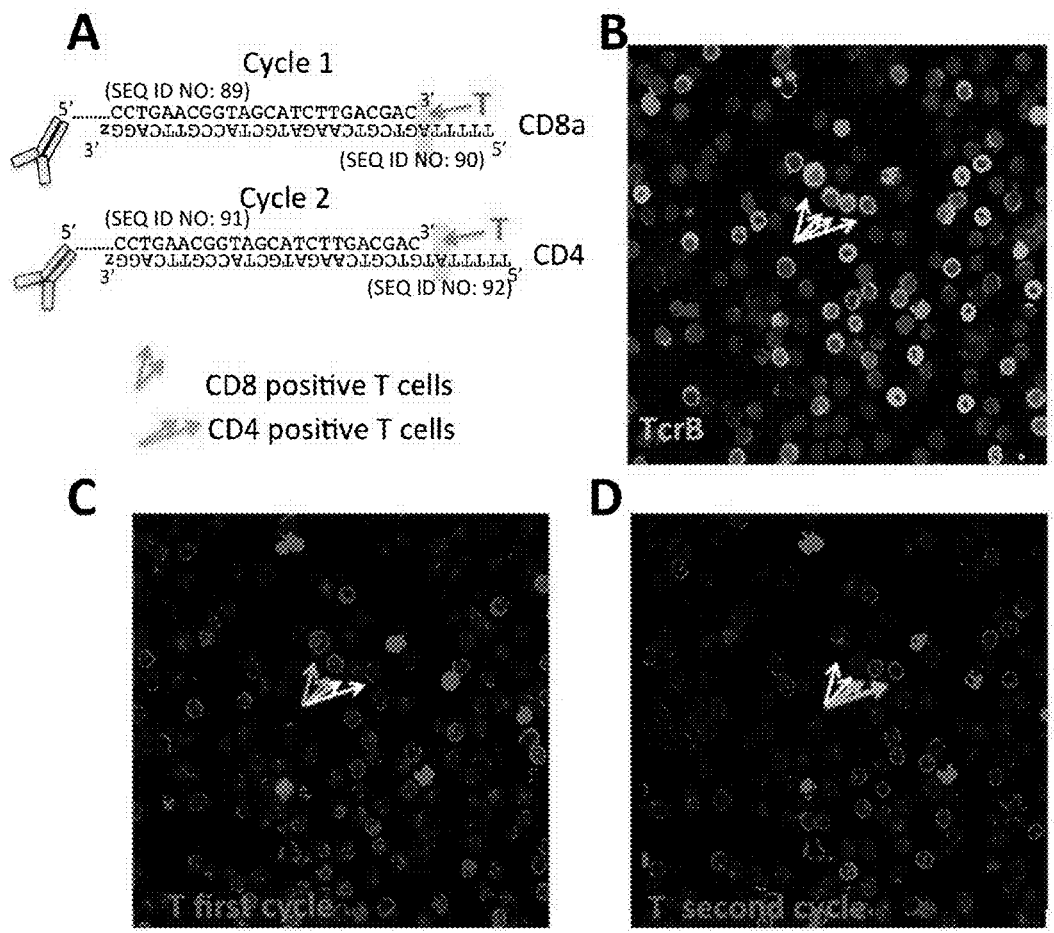
FIGS. 13A-13D show schematic illustration of two capture agents CD4 and CD8 linked to oligonucleotide duplexes (panel A) and data obtained from a multiplexed method whereby staining by this capture agents was sequentially detected on spleen cells smeared on a slide using a "reversible terminator" method (panels C-D). SEQ ID NOS: 89-92.

In this implementation of the method, the planar sample can be co-stained simultaneously using a panel of capture agents, each labeled with one oligonucleotide duplex designed according to the strategy outlined on FIG. 3. The duplexes are designed in such a way that each antibody has the same upper strand sequence linked, covalently or through streptavidin, to an antibody through the 5' end. The lower strand changes from antibody to antibody. In this implementation, the general formula for the lower strand is 3'-dideoxydC-sequence-complimentary-to-upper-strand $G_n$A/T/C-5'. One type of lower strand base (nucleotide G in this example) is reserved for step-wise progression and its complementary pair on the upper strand is never used in labeled form. The other three bases are complementary to labeled nucleotides and can be used to identify three capture agents per cycle. In a more general case the general formula for the lower strand is 3'-dideoxydC-sequence-complimentary-to-upper-strand-X-$N_1/N_2/N_3$-5' where $X_i$ of X is any nucleotide excluding one reserved for "walking base" of this particular cycle and X is any base as shown on FIG. 5B. This design ensures that: a) no two antibody species contain the same duplex and b) only three different capture agents are detected at a time. Each cycle includes: (a) a labeling step in which the three capture agents are labeled and duplexes on the rest are extended one base at a time, (b) an imaging step and (c) a destaining/deprotection step. During cycle to cycle transition the added fluorescent labels from the previous cycle are inactivated by any of the suitable methods, including but not limited to: cleavage of fluorophore off the nucleotide (if the labeled nucleotide is linked to the fluorophore through a cleavable linker); peroxide based bleaching; photobleaching; chemically-assisted photobleaching; labeled base replacement by exo+ polymerase, etc. After or simultaneously with inactivation of the fluorophores added in the previous reaction, the unlabeled "extension" nucleotide that has been added to the remainder of the capture agents is activated by cleavage of the protective group off its 3' end. Cleavage of the protective group, in turn, allows that nucleotide to be extended in the next cycle. Since the A, T and C are reserved for incorporation of a labelled nucleotide, those nucleotides only occur at the end of each lower strand of the duplex. This approach is based on the chemical nature of reversible terminators, which precludes upper strand extension for more than one nucleotide at a time even on polyG stretches of the lower strand. Optionally, a quencher labeled nucleotide can be incorporated following the labeled nucleotide. The performance of "reversible terminator method" as exemplified in sequential detection of CD4 and CD8 positive T-cells in smears of mouse splenocytes is illustrated in FIG. 13 A-D.

Missing Base Method

This implementation of the method relies on a "missing" base design in which, in each cycle, two labeled and one unlabeled nucleotides are added to the reaction, and the "missing base" prevents the primers from being extended by more than a single nucleotide.

This method can be implemented using a composition comprising a plurality of capture agents that are linked to double stranded oligonucleotides, as illustrated in FIG. 4. In these embodiments, the top strand of the double stranded oligonucleotide is linked to the capture agent and is same for each antibody, and the sequence of the bottom strand varies between capture agents. As shown in FIG. 4, the 5' end of the lower strand of the double-stranded oligonucleotide (which forms the overhang) is of the general formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C.

Also a more general formula 3'-$YN_1/N_2$-5', wherein $N_1$, $N_2$, $N_3$ and $N_4$ are different nucleotides selected from G, A, T and C and Y is a nucleotide sequence of length n (n is 0, 1 or more) composed of alternating random length stretches of bases $N_3$ and $N_4$ such that the order number of $N_3$-stretches is odd and of $N_4$ stretches is even, may be applicable in this method In certain embodiments, this method may comprise: (a) incubating a planar sample with a multiplex antibody composition in which the overhangs are of the formula (3'-$YN_1/N_2$-5') described in the prior paragraph; under conditions by which the capture agents specifically bind complementary sites in the planar sample; (b) cross-linking the capture agent to the planar sample; (c) contacting the planar sample with a polymerase and a nucleotide mix that comprises fluorescent nucleotides that are complementary to $N_1$, and $N_2$, an unlabeled nucleotide that is complementary to $N_3$ and no nucleotide that is complementary to $N_4$; and (d) reading, using fluorescence microscopy, a fluorescent signal generated by addition of a nucleotide to some but not all of the capture agents. This cycle may be repeated by (e) inactivating the fluorescent signal, (f) blocking the sample and contacting the planar sample with a polymerase and an unlabeled nucleotide that is complementary to $N_4$; and repeating steps (c) (d). In certain embodiments, the method may comprise repeating steps (c), (d), (e) and (f) multiple times.

This method can be implemented using a capture agent composition that comprises: a first antibody linked to a first double stranded oligonucleotide, wherein the first double stranded oligonucleotide comprises a single nucleotide 5' overhang comprising base $N_1$; a second antibody linked to a second double stranded oligonucleotide, wherein the second double stranded oligonucleotide comprises a single nucleotide 5' overhang comprising base $N_2$; a third antibody linked to a fourth double stranded oligonucleotide, wherein the third double stranded oligonucleotide comprises a two nucleotide 5' overhang, wherein the first from the 3' position of the overhang comprises base $N_4$ and the second position comprises $N_1$; and a fourth antibody linked to a fourth double stranded oligonucleotide, wherein the fourth double stranded oligonucleotide comprises a two nucleotide 5' overhang, wherein the first position of the overhang comprises base $N_4$ and the second position comprises base $N_2$, wherein $N_1$, $N_2$, $N_3$ and $N_4$ are different nucleotides selected from G, A, T and C. An example of such a population of capture agents is shown in FIG. 4.

In certain implementations, the composition may also contain a fifth antibody linked to a fifth double stranded oligonucleotide, wherein the fifth double stranded oligonucleotide comprises a multiple nucleotide 5' overhang, wherein the first position of the overhang comprises base $N_4$, the second position comprises base $N_3$, and the third position comprises $N_1$ or $N_2$.

Overall there is no theoretical limits to the number of co-detected complementary sites, e.g., antigens, both in the case of "reversible terminator" and of "missing base" approach The missing base approach does not use reversible terminators. Instead, extension of a single nucleotide is ensured by using two interchanging bases (e.g., T and C as shown in FIG. 4 instead of the corresponding G in the "reversible terminators" approach) and adding only one of the two dNTPs at a time in the primer extension reaction. After the incorporation of the first nucleotide, the absence of the second dNTP causes strand elongation to stall, thereby ensuring that the primers are extended by only a single nucleotide. As in the previous strategy, all complementary sites can be co-stained simultaneously using capture agents, each labeled with a specific oligonucleotide duplex.

In this embodiment, the duplexes can be designed using the strategy shown in FIG. 4, i.e., in such a way that each antibody has the same upper stand oligonucleotide sequence linked to it via covalent bond or through a streptavidin-biotin interaction. In this implementation, the lower strand changes from antibody to antibody. In this method, the general formula for the lower strand is 3' ddC-sequence-complimentary-to-upper-strand-YA/$N_2$-5' where Y is composed of bases T and C such that T can be found only in even and C only at odd positions. Or in the more general case 3'-$YN_1/N_2$-5', wherein $N_1$, $N_2$, $N_3$ and $N_4$ are different nucleotides selected from G, A, T and C and Y is a nucleotide sequence of length n (n is 0, 1 or more) composed of alternating random length stretches of bases $N_3$ and $N_4$ such that the order number of $N_3$-stretches is odd and of $N_4$ stretches is even. In the first simple implementation two base pairs of the lower strand (T and C as in exemplary design on FIG. 4) are reserved for step-wise progression and their complementary pair on the upper strand is never labeled. The other two bases are complementary to labeled nucleotides and can render the staining with two different capture agents per cycle. Such design ensures that a) no two capture agents contain the same duplex and b) only two different antibody are read per cycle. In this implementation, each cycle can have three steps: a labeling step in which the two capture agents are labeled by incorporation of fluorescent dNTPs and all of the other duplexes are extended one base at a time, an imaging step, and a de-staining/reactivation step.

Figure 15:
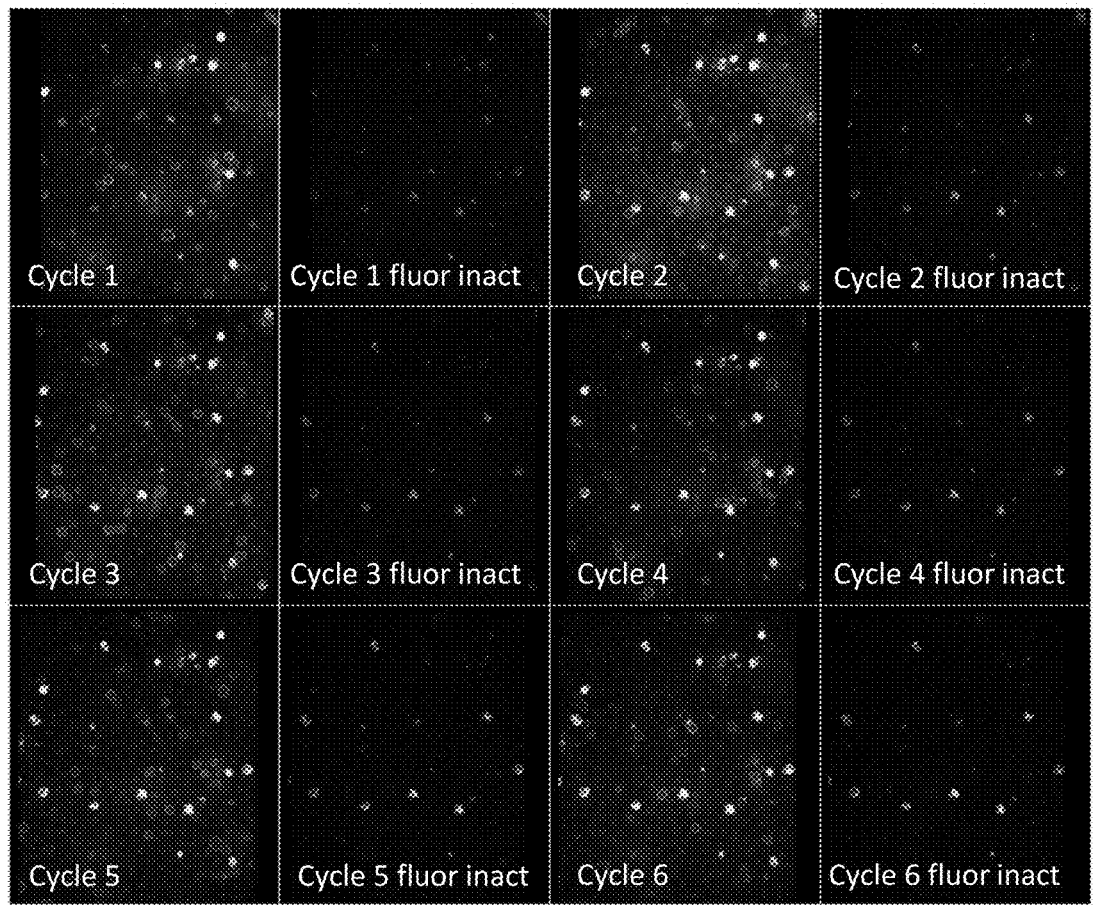
FIG. 15 is 12 panels of images showing the first 6 cycles of rendering the 30 populations barcoded by CD45 (as per scheme on FIG. 14). Two populations were co-detected per cycle of rendering. In each cycle control image was acquired after fluorescence inactivation.

During cycle-to-cycle transition the labeled capture agents from the prior cycle can be bleached/destained in the same way as described above. Optionally, instead of bleaching, a quencher labeled nucleotide can be incorporated after the labeled base. Because, in this embodiment, the position that is labeled is the last position in the overhang, the labeled capture agents from prior cycle cannot be re-labeled in later cycles because all nucleotide positions in the overhang have been filled in. The performance of "reversible terminator method" as exemplified in sequential detection of CD4 and CD8 positive T-cells in smears of mouse splenocytes is illustrated in FIG. 13, 15 and FIG. 16.

Exemplary Method 2

Figure 7:
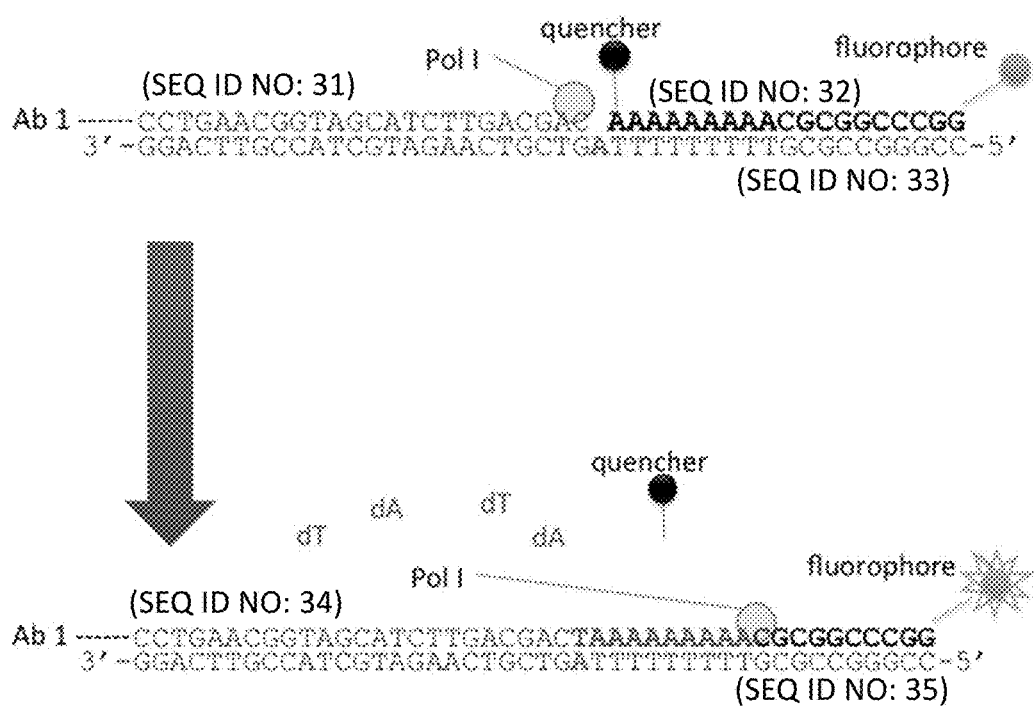
FIG. 7 schematically illustrates an example of a detection method that relies on removing a quencher from a labeled oligonucleotide by nick translation. SEQ ID NOS: 31-35.
Figure 8:
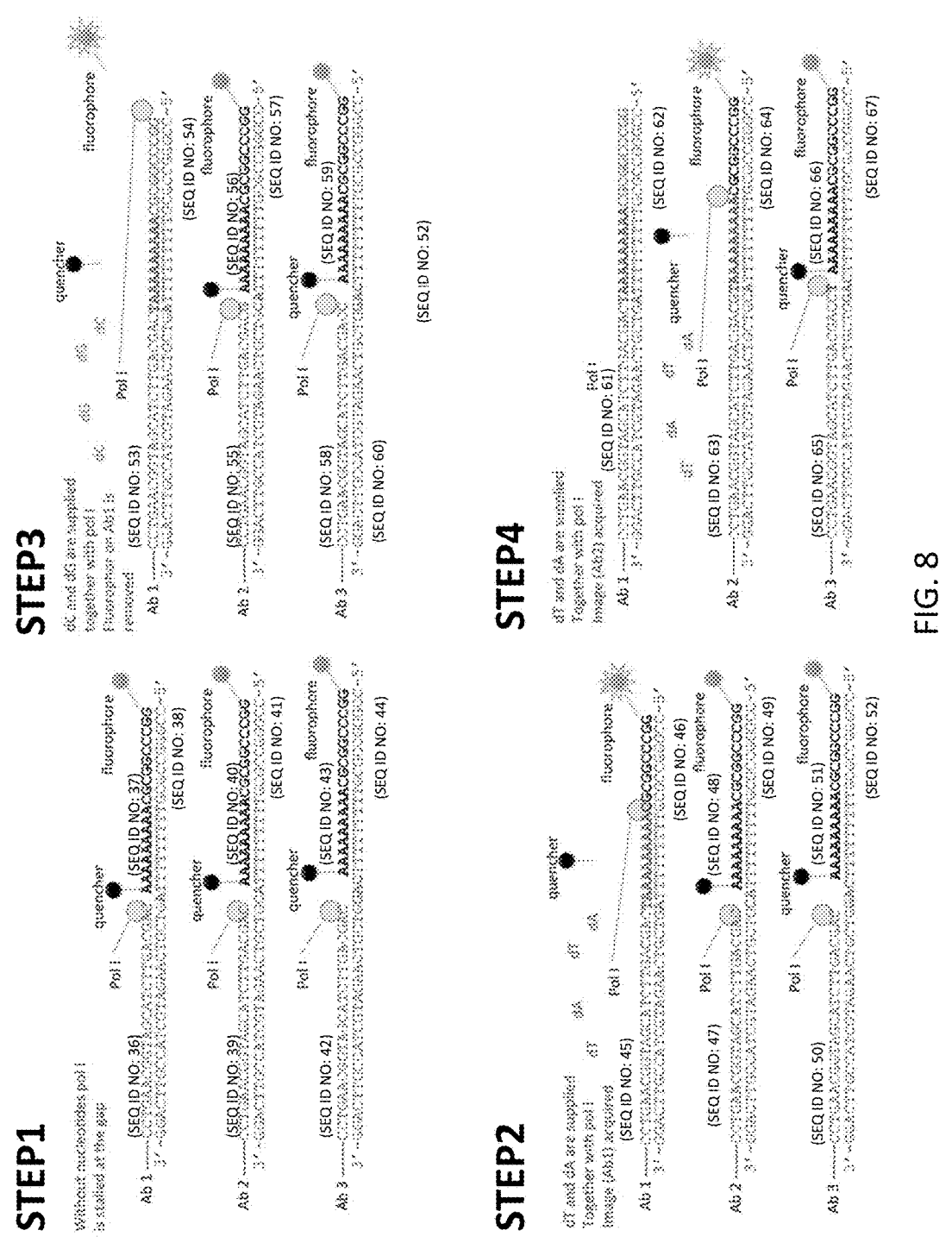

In this method, extension of a primer by nick translation removes a quencher from a fluorescently labeled "detector" oligonucleotide that is hybridized to the lower strand oligonucleotide in such a way that is positioned downstream from the upper strand primer. The principles of this method are illustrated in FIG. 7. A multiplexed version of this method is shown in FIG. 8.

In certain embodiments, the multiplexed implementations may comprise: (a) incubating the planar sample with a plurality of capture agents that are linked to a double-stranded oligonucleotide; (b) crosslinking the capture agents to the planar sample; (c) extending a primer that is hybridized to the oligonucleotide of a first set of capture agents of the plurality, thereby generating a first set of fluorescent signals (e.g., by removing the quencher from a labeled oligonucleotide that is hybridized to the oligonucleotide downstream from the primer); (d) reading the first set of fluorescent signals using fluorescence microscopy; (e) inactivating the fluorescence; (f) extending a primer that is hybridized to the oligonucleotide of a second set of capture agents of the plurality, thereby generating a second set of fluorescent signals (e.g., by removing the quencher from a labeled oligonucleotide that is hybridized to the oligonucleotide downstream from the primer); (g) reading the second set of fluorescent signals using fluorescence microscopy; and (h) comparing the images produce in steps (d) and (g).

In this method, the architecture of the double-stranded oligonucleotides linked to the capture agent has a specific design which is effectively enabling rendering of the capture agent binding pattern by "nick translation". In particular the duplex of the upper strand and the lower strand oligo with long 5' overhang of the lower strand is further hybridized to a small detector oligonucleotide labeled both by fluorescent and the quencher. There is a predesigned gap between the initial upper strand and the upper strand detector oligo. During cyclic staining this gap is "walked" by either "reversible terminator" or "missing base" (similar to described in previous sections) until the gap is reduced to a single base nick. Extension and progression through the nick on the upper strand by "nick translating" polymerase such as DNA pol I removes the quencher from some but not all of the quenched fluorescently labeled oligonucleotides, thereby generating a fluorescent signal for some but not all of the capture agents.

In some embodiments the method generally comprises: (i) labeling a planar sample with: i. a first antibody, wherein the first antibody is linked to a first oligonucleotide duplex comprising, lower strand oligonucleotide with a unique sequence hybridized thereto: (i) an oligonucleotide upper strand "primer" and (ii) a labeled upper strand oligonucleotide comprising a 5' quencher at a site that is downstream from the primer; and a fluorophore downstream from the quencher and ii. a second antibody, wherein the second antibody is linked to a second oligonucleotide duplex comprising, lower strand oligonucleotide with unique sequence hybridized thereto: (i) an oligonucleotide upper strand "primer" and (ii) an upper strand oligonucleotide labeled both by fluorophore and a quencher; wherein the gap between the 3' end of the primer and the 5' end of the labeled oligonucleotide is different for the first and second oligonucleotides; (ii) incubating the tissue sample with a first nucleotide mix and a polymerase, thereby removing the quencher from only the labeled oligonucleotide that is hybridized to the first oligonucleotide and producing a first fluorescent signal; (iii) reading the first fluorescent signal using fluorescence microscopy; (iv) inactivating the fluorescent signal by further progression of nick-translating polymerase; (v) incubating the tissue sample with a second nucleotide mix and a polymerase, thereby removing the quencher from only the labeled oligonucleotide that is hybridized to the second oligonucleotide and producing a first fluorescent signal; and (vi) reading the second fluorescent signal from the planar sample using fluorescence microscopy.

FIGS. 7 and 8 show an example of this method. The multiplexing method shown in FIG. 8 has the following steps:

Step 1: The planar sample is stained by capture agents that are coupled to a DNA double-stranded oligonucleotide chemically or through streptavidin (as described in FIG. 1) such that the top strand of the duplex contains a nick or a single base deletion followed by a nucleotide stretch bordered by a fluorophore and its quencher on two ends ("molecular beacon" or Taqman based design).

Step 2: Staining pattern is rendered by a nick-translation reaction carried out by any 5' exo+ polymerase such as DnaPolI Klenow fragment in the presence of a single letter (A as in FIG. 5 for example). Nick translation removes the quencher but stops before removing the part of the duplex with the fluorophore.

Step 3: For rendering of other staining reagents, the fluorescence is removed by continuing nick translation in the presence of the letters of the stretch bearing the fluorophore.

Step 4: When multiplexing is desired, multiplexing can be achieved by special design of oligo duplexes attached to detection reagents. In particular each antibody set (two or three per cycle) has a gap of an increasing length between the top strand priming and the detector oligonucleotide. This sequence gap on the strand bearing the quencher/fluorophore pair is filled up to final nick in such a way that single base is extended per cycle, similar to how it is achieved in method 1 (see FIG. 8).

Exemplary Method 3

In this implementation, the method comprises rending antibody staining by primer extension with a fluorophore labeled base or otherwise reading a FRET signal generated by energy transfer between a first fluorescent nucleotide added to the primer by primer extension and a second nucleotide that is present in the oligonucleotide FIG. 10. The principles of this method are illustrated in FIG. 9A. The multiplexing is achieved by removing the extension priming oligo by melting the duplex or by exonuclease and reannealing another primer oligo which is extendable on a different antibody. A multiplexed version of this method is shown in FIG. 9B. In certain embodiments, the multiplexed implementations may comprise: (a) incubating the planar sample with a plurality of capture agents; (b) cross-linking the capture agents to the planar sample; (c) extending a primer that is hybridized to the oligonucleotide of a first set of capture agents of the plurality (e.g., wherein the 3' end of the first primer anneals to only the oligonucleotide of the first population), thereby generating a first set of fluorescent signals; (d) reading the first set of fluorescent signals using fluorescence microscopy; (e) inactivating the fluorescence; (f) extending a primer that is hybridized to the oligonucleotide of a second set of capture agents of the plurality (e.g., wherein the 3' end of the first primer anneals to only the oligonucleotide of the second population), thereby generating a second set of fluorescent signals; (g) reading the second set of fluorescent signals using fluorescence microscopy; and (h) comparing the images produce in steps (d) and (g).

In certain embodiments, this method comprises: (a) incubating the planar sample with (i) a first antibody that is linked to a first labeled oligonucleotide and (ii) a second antibody that is linked to a second labeled oligonucleotide, (b) cross-linking the capture agents to the planar sample; (c) hybridizing the first and second labeled oligonucleotides with a first primer, wherein the 3' end of the first primer anneals to only the first labeled oligonucleotide; (d) extending the primer with a fluorescent nucleotide; (e) reading, by fluorescence microscopy, a FRET signal generated by energy transfer between the label of the first oligonucleotide and the fluorescent nucleotide added to the first primer; (f) inactivating the fluorescent nucleotide added to the first primer; (g) hybridizing the first and second labeled oligonucleotides with a second primer, wherein the 3' end of the second primer anneals to only the second labeled oligonucleotide; (h) extending the second primer with a fluorescent nucleotide; and (i) reading, by fluorescence microscopy, a FRET signal generated by energy transfer between the label of the second oligonucleotide and the fluorescent nucleotide added to the second primer.

FIGS. 9-10 shows an example of this method. The method shown in FIGS. 8-11 has the following steps:

Step 1: The planar sample is stained using a capture agent that is coupled to a single stranded oligonucleotide. The oligonucleotide could be either unlabeled or labeled by FRET acceptor (e.g. Cy5) fluorophore on the 3' end.

Step 2: The binding pattern can be determined by an on-slide hybridization of a complementary probe followed a primer extension reaction in which a fluorescently labeled nucleotide fills in the overhang in the extended strand. In this example (see FIG. 10) the extended base is labeled by a FRET donor (e.g. Cy3), which can increase the signal to noise ratio. If the oligonucleotide that is linked to the capture agent is unlabeled, then the fluorescent emission of the nucleotide that has been incorporated by DNA synthesis can be detected directly, without FRET FIG. 9.

Step 3: The binding pattern of other capture agents can be determined by removing the fluorescence by cleavage of lower strand by exo+ DNA polymerase such as Vent (FIG. 9). Alternatively, the fluorescence can be removed by raising the temperature beyond the melting point of the DNA strands or by one of the de-staining techniques described previously.

Figures 11A, 11B, 11C:
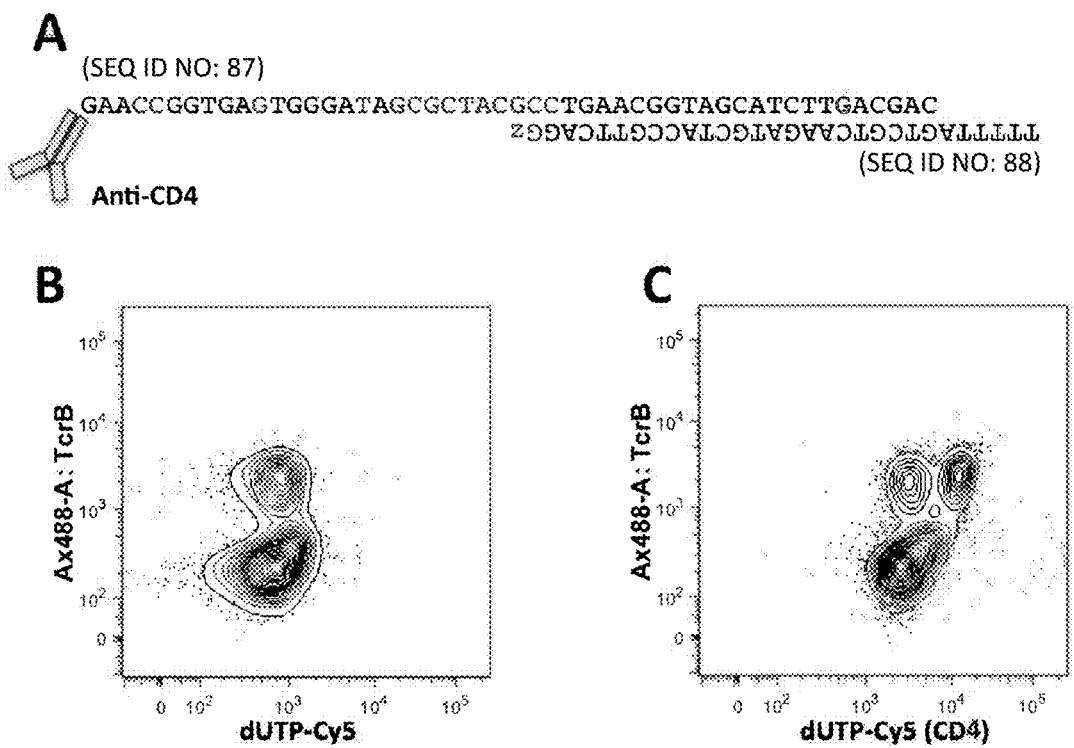
FIGS. 11A-11C shows an anti-CD4 antibody linked to oligonucleotide duplex designed for rendering staining by primer extension (panel A) and data obtained from labeled population of spleen cells in suspension in the absence of polymerase (panel B) and in the presence of polymerase (panel C). SEQ ID NOS: 87 and 88.

Step 4: Multiplexing can be achieved by staining of the sample with a library of capture agents each labeled with specific oligonucleotides and cycling through Steps 1-3, as described above, each time using a different detection oligonucleotide that is complementary to one of the capture agent-conjugated oligonucleotides. Only duplexes where primers are annealed specifically will be properly extended (FIG. 11). In these embodiments, each primers is designed so that its 3' end hybridizes to only one of the oligonucleotides that are linked to a capture agent.

Utility

The planar sample may be a section of a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In certain embodiments, capture agents specifically bind to biomarkers, including cancer biomarkers, that may be proteinaceous or a nucleic acid. Exemplary cancer biomarkers, include, but are not limited to carcinoembryonic antigen (for identification of adenocarcinomas), cytokeratins (for identification of carcinomas but may also be expressed in some sarcomas), CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas) and CD3 (for identification of T-cell lymphomas).

The above-described method can be used to analyze cells from a subject to determine, for example, whether the cell is normal or not or to determine whether the cells are responding to a treatment. In one embodiment, the method may be employed to determine the degree of dysplasia in cancer cells. In these embodiments, the cells may be a sample from a multicellular organism. A biological sample may be isolated from an individual, e.g., from a soft tissue. In particular cases, the method may be used to distinguish different types of cancer cells in FFPE samples.

The method described above finds particular utility in examining planar samples using a plurality of antibodies, each antibodies recognizing a different marker. Examples of cancers, and biomarkers that can be used to identify those cancers, are shown below. In these embodiments, one does not need to examine all of the markers listed below in order to make a diagnosis.

| | |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel - Female) | CK7, CK20, mammaglobin, ER, TTF1, CEA, CA19-9, S100, synaptophysin, and WT-1. |

| | |
|---|---|
| Carcinoma Unknown Primary Site, Male (CUPS IHC Panel - Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma IHC Panel | CDX2, CK 20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. |

In some embodiments, the method may involve obtaining an image as described above (an electronic form of which may have been forwarded from a remote location) and may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the image may be analyzed by an MD or other qualified medical professional, and a report based on the results of the analysis of the image may be forwarded to the patient from which the sample was obtained.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment, the sample pair is represented by undifferentiated cells, e.g., stem cells, and differentiated cells.

The images produced by the method may be viewed side-by-side or, in some embodiments, the images may be superimposed or combined. In some cases, the images may be in color, where the colors used in the images may correspond to the labels used.

Cells any organism, e.g., from bacteria, yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

Experimental

Preliminary Data

Figures 12A, 12B, 12C, 12D:
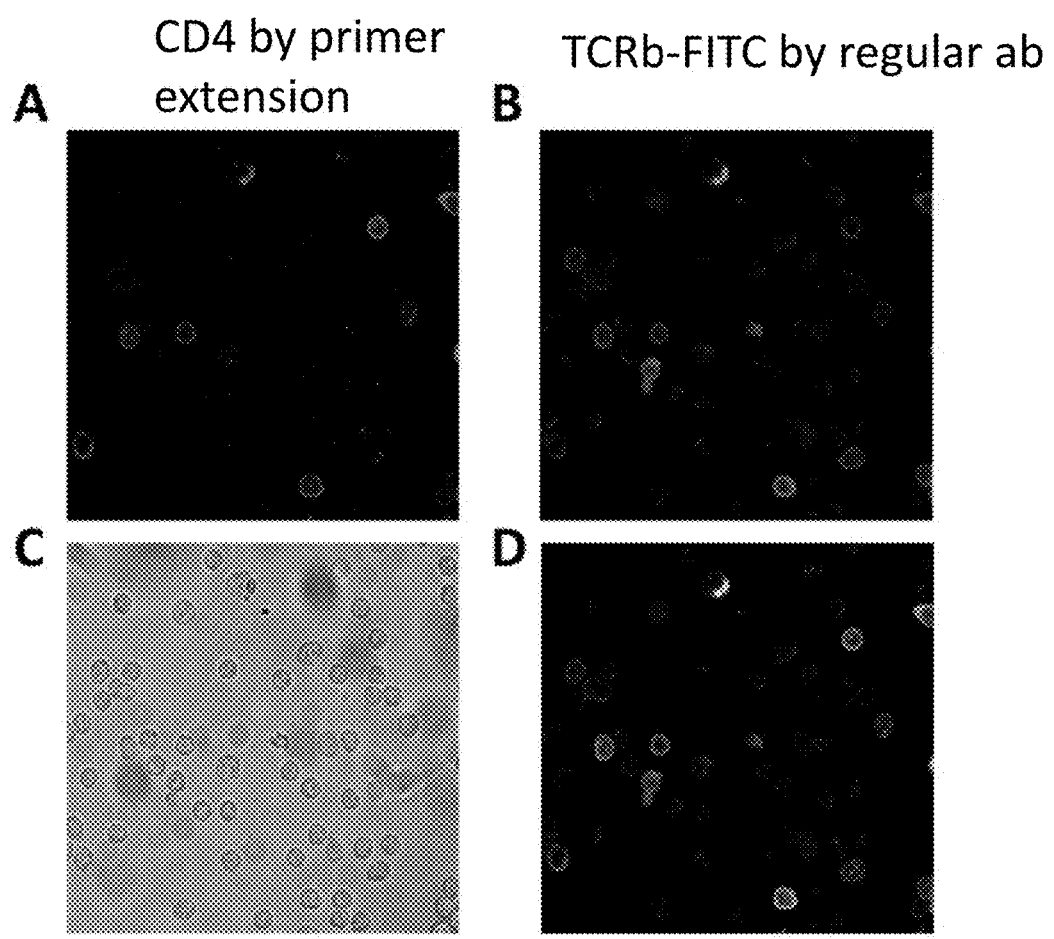
FIGS. 12A-12D shows data obtained from labeling by primer extension a population of spleen cells preattached on the slide. Cells were co-stained with "regular" TCRb-FITC antibody and CD4 antibody linked to oligonucleotide duplex designed for rendering staining by primer extension.

To explore the possibility of in situ staining by primer extension expression of CD4 was visualized in mouse spleen cells in suspension (FIG. 11) or immobilized on a slide. (FIG. 12). To visualize the T lymphocytes spleen cells were co-stained with conventional TcrB-Ax488 antibody. Both samples were stained with CD4 antibody conjugated to oligo duplex as in (FIG. 11 A). No Klenow polymerase was added in control samples which results in no separation of TcrB positive T-cells into subsets (FIG. 11 B). When Klenow polymerase was supplied. CD4 positive T-cells could be observed as a Cy5 positive subset of TcrB positive T-cells (FIG. 11 C and FIG. 12). Clear membrane staining pattern was observed by confocal imaging of cells stained on-slide (FIG. 12 A). Taken together this data shows that on-slide primer extension reaction can be used for rendering the capture agent binding pattern FIG. 11. Flow cytometric analysis of mouse spleen cells stained by primer extension. Mouse spleen cells were fixed and permeabilized with methanol as done for intracellular protein staining. Cells were co-stained with conventional TcrB-Ax488 antibody and CD4 antibody conjugated to oligo duplex as in (A). After staining cells were either incubated in extension buffer with dUTP-Cy5 without (B) or with (C) Klenow exo⁻ polymerase. Note that TcrB positive T-cells in (B) are indicated by Ax-488 staining. Dependent upon the addition of Klenow, TcrB positive CD4 positive T-cells are seen as a Cy5 positive subset of TcrB positive T-cells in (C).

FIG. 12. On-slide analysis of mouse spleen cells stained by primer extension. Mouse spleen cells were fixed and permeabilized with methanol as done for intracellular protein staining. Cells were attached to poly-Lysine coated slide and co-stained with conventional TcrB-Ax488 antibody and CD4 antibody conjugated to oligo duplex as in FIG. 12 A. After staining, cells were incubated in extension buffer with dUTP-Cy5 Klenow exo⁻ polymerase and visualized by confocal microscopy. Shown are DIC image in C, Cy5 channel in A, Ax488 channel in B and merged Ax488 and Cy5 channels in D. Note that only a subset of TcrB-Ax488 positive T-cells in (B) are rendered Cy5 positive CD4 positive T-cells by primer extension as seen in (A). The membrane pattern of CD4 points to specificity of staining by primer extension as it takes place at a particular expected subcellular localization.

Figure 14:
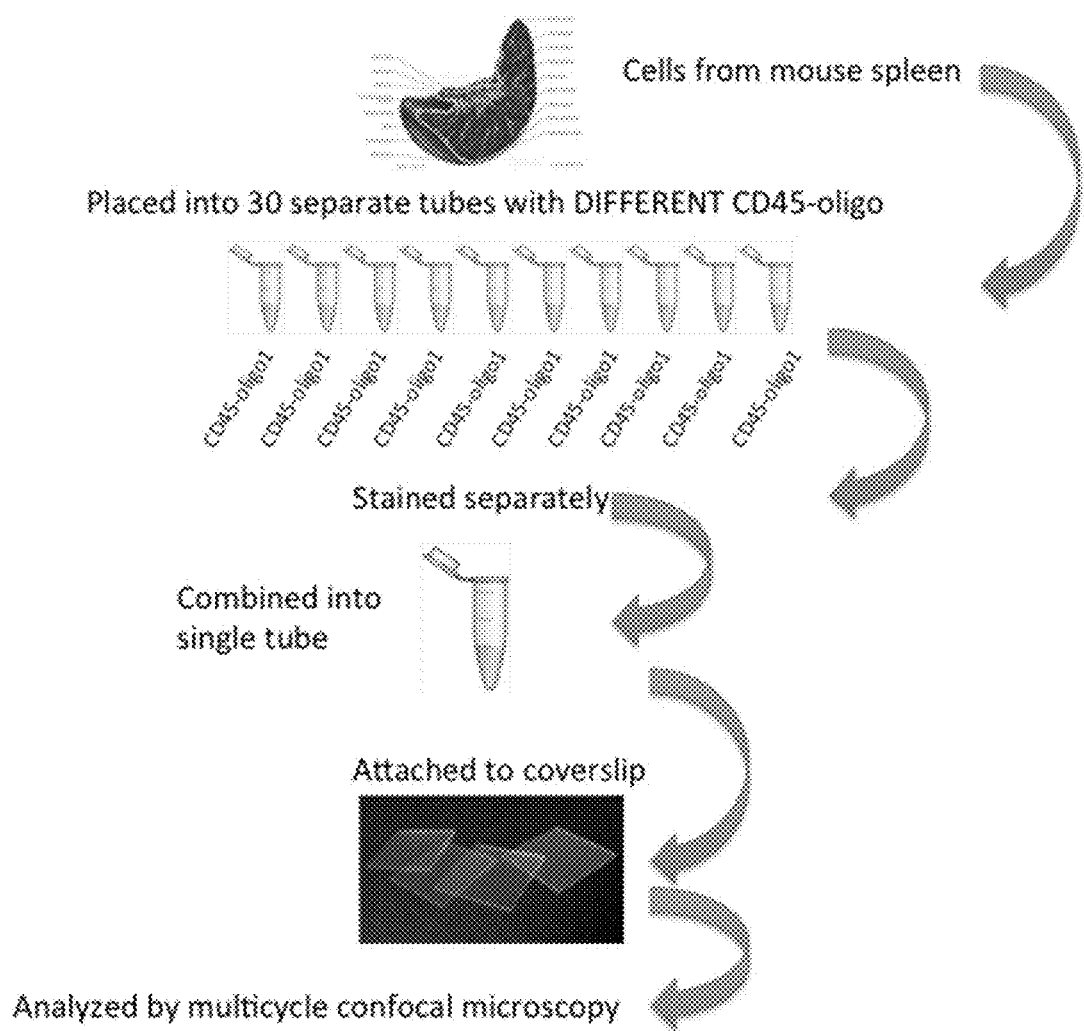
FIG. 14 shows a chematic diagram of an experiment testing multiplexed staining by "missing base" approach. Mouse spleen samples were barcoded by pan-leukocytic CD45 antibody conjugated to per sample specific oligonucleotide duplexes. Samples were mixed after staining and mixture was resolved by sequential rendering of CD45-oligonucleotide variants.

To prove the possibility of multiplexed detection of several antigens by primer extension, the expression of CD4 and CD8 was co-analyzed in mouse spleen cells immobilized on a slide by Method 1 and, specifically, the multiplexing approach based on "reversible terminators". The cells were simultaneously stained by CD4 and CD8 antibodies conjugated to oligo duplexes as in (FIG. 14 A) simultaneously. Two cycles of rendering were performed such that CD8 was visualized in the first cycle (FIG. 14 C) and CD4 in the second (FIG. 14 D). Cells were counterstained with TcrB-Ax488 to delineate T-lymphocytes in the spleen cells. As expected CD4 positive cells were rendered as a subset of TcrB positive T-cells mutually exclusive with CD8-positive subset of T-lymphocytes (FIG. 14 A-D). Our data suggests that rendering antibody staining by polymer (DNA-duplex) extension is an approach enabling sensitive antigen detection and multiplexing.

FIG. 13. Two cycle analysis of CD4 and CD8 staining in mouse spleen using Method 1 with reversible terminators. Mouse spleen cells were fixed and permeabilized with methanol as done for intracellular protein staining. Cells were attached to poly-Lysine coated slide and co-stained with conventional TcrB-Ax488 antibody and a mixture of CD4 and CD8 antibodies conjugated to oligos as indicated on (A). For the first cycle of staining the cells were incubated in extension buffer with Illumina reversible terminators and Klenow exo⁻ polymerase and visualized by confocal microscopy (C). Following the imaging after the first cycle, cells were destained by Illumina cleavage buffer containing TCEP. Following destaining-terminator reactivation, cells were again incubated in extension buffer with Illumina reversible terminators and Klenow exo⁻ polymerase and visualized by confocal microscopy (D) Note that four T-cells identified by high levels of TcrB and marked by four white arrows on (B). It becomes evident after the first cycle of staining that two of these cells are CD8a positive (marked by purple arrows on (C). Second cycle of staining reveals that the other two cells are CD4 positive (marked by green arrows on (D). The expected mutual exclusivity of CD4 and CD8a as well as membrane pattern of incorporated labeled nucleotide further supports the specificity of staining by cycles of primer extension.

The "missing base" multiplexing approach was tested on a model of heterogeneous tissue containing multiplicity of distinct cellular subsets (FIG. 14). To this end leukocytes from homogenized mouse spleen were divided into 30 samples. 30 different versions of CD45 were made by conjugating purified CD45 to common upper strand oligo and then separately annealing 30 different lower strand oligonucleotides designed to create overhangs that can be sequentially rendered (two per cycle) in the multiplexed version of "missing base approach". The samples were individually stained (barcoded) by 30 CD45 antibody conjugates, the unbound CD45 was washed off the barcoded samples were mixed and attached to a slide. The staining of this mixture of pseudotyped cells was rendered by "missing base" approach. Six first cycles (12 populations, 2 red and green per cycle) as well as inactivation of fluorescence by cleaving the fluorophore off the modified base by TCEP between the cycles is shown on FIG. 15. As can be seen no same two cells are stained in each cycle and between the cycles proving that on-cell primer extension reliably renders the specific antibody staining.

Materials and Methods

Spleen cells fixed in 2% formaldehyde, permeabilized and stored in methanol at −80 were spun from methanol, resuspended and washed with buffer 4 (10 mM Tris & 5, 10 mM MgCl2, 150 mM NaCl, 0.1% Triton×100) for 5 min on a rotator. To block against non-specific binding of ab-oligo complexes cells were further spun, resuspended in 1 ml PBS, 0.5% BSA (SM) and supplemented up to additional 0.5M NaCl (0.9 ml SM+100 ul 5M NaCl). 20 ul of sheared ssDNA (10 mg/ml), 50 ul of mouse IgG (10 mg/ml) and 20 ul of 0.5M EDTA were further added to 1 ml of cells and the mix was incubated for 30 min on a rotator. For staining cells were redistributed into 30 250 ul tubes (PCR strip tubes is a convenient choice for that matter) with premade antibody/oligo complexes (0.2 ug of CD45-146 complex was annealed with 1 ul of specific oligo (147 etc) per tube 30 min at 40 C) and incubated for 1 h with rotation. Cells were washed in (PBS, 0.1% Triton 0.5M salt 5 mM EDTA) twice, placed on poly-lysine treated glass coverslips, allowed to stand/attach for 10 min and further fixed with 5 mM BS3 (7.4 mg per 4 ml) in PBS, 0.1% Triton, 0.5M NaCl, 5 mM EDTA for 1 hour.

Staining was rendered in cycles. For odd cycles (1, 3, 5, 7, 9, 11, 13, 15) coverslips were incubated for 2 min in dG/dU mix (150 nM dG, 150 nM dUssCy5, 150 nM dCssCy3, 25 ul NEB exo-Klenow per ml in buffer#4 (10 mM Tris 7.5, 0.5M NaCl, 0.1% Triton×100, 10 mM MgCl2)), washed twice with 405 (buffet#4 supplemented up to 0.65M NaCl); and imaged by confocal microscopy. Following imaging the fluorophores were cleaved off cells by incubation in 50 mM TCEP for 2 min in buffer 405E (10 mM Tris 7.5, 0.5M NaCl, 0.1% Triton×100, 5 mM EDTA). After cleavage cells were washed in 405E and blocked for 1 min in iodoacetamide solution (FRESHLY made 100 mM iodoacetamide in buffer 405E). The blocking solution was removed by two washes with buffer#4. Before proceeding to next cycle cells were again imaged by confocal microscopy. Even cycles (2, 4, 6, 8, 10, 12, 14) were performed same as odd cycles except for substitution of dG with dA in labeling step and extension of cleavage to 4 min at room temperature.

Results

In order to test the performance and multiplexing capacity of "missing base" method the following model approach was employed FIGS. 14 and 15. Mouse CD45 antibody was chemically conjugated to an "upper strand" oligo (oligo id-146). The conjugated antibody was further divided and separately annealed (by 30 min co-incubation at 40 C) to 30 different "lower strand" oligonucleotides—thus effectively creating 30 different species of CD45 antibody. The 30 "lower strand" oligonucleotides were designed in accordance with "missing base" strategy and in addition in such a way that 2 antibodies could be rendered per cycle using two bases (dUTP and dCTP) reversibly (through s-s linker) coupled with distinct fluorophores (Cy5 and Cy3). 30 samples of homogenized mouse spleen have been "barcoded" with these CD45-oligo duplex complexes such way that majority of cells in each sample became labeled with a particular CD45-upper/lower oligo combination. Following staining and washing the samples were combined to mimic a tissue with 30 different cellular subsets. The mixture was smeared on a slide and rendered by cycling staining with a "missing base" approach such that two subsets per staining cycle were co-visualized on different imaging channels.

What is claimed is:

1. A method for stabilizing the binding of a plurality of oligonucleotide-linked antibodies to a sample, comprising:
   (a) binding the sample with a plurality of antibodies that are linked to oligonucleotides; and
   (b) crosslinking the antibodies directly to the sample using a chemical crosslinker.

2. The method of claim 1, wherein the chemical cross-linker is bifunctional cross-linker.

3. The method of claim 1, wherein the chemical cross-linker is an amine-to-amine cross-linker.

4. The method of claim 1, wherein the chemical cross-linker comprises formaldehyde.

5. The method of claim 1, wherein the chemical cross-linker comprises a disuccinimidyl crosslinker.

6. The method of claim 1, wherein the sample is planar.

7. The method of claim 1, wherein the sample is a tissue section.

8. The method of claim 1, wherein the sample is a formalin-fixed paraffin embedded (FFPE) tissue section.

9. The method of claim 1, wherein the sample is a tissue biopsy.

10. The method of claim 1, wherein the antibodies bind to diagnostic markers in the sample.

11. The method of claim 1, wherein the plurality of antibodies comprises a first antibody that is linked to a first oligonucleotide and a second antibody that is linked to a second oligonucleotide.

12. The method of claim 1, wherein the plurality of antibodies comprises at least 10 antibodies, each linked to a different oligonucleotide.

13. The method of claim 1, wherein the plurality of antibodies comprises at least 50 antibodies, each linked to a different oligonucleotide.

14. The method of claim 1, wherein the oligonucleotides are double-stranded.

15. The method of claim 1, wherein the oligonucleotides are single-stranded.

16. The method of claim 1, further comprising
   (c) labeling some not all of the antibodies with a fluorescently label after they are cross-linked to the sample in step (b).

17. The method of claim 1, wherein the antibodies are monoclonal antibodies.

18. The method of claim 1, wherein the antibodies are not fluorescently labeled prior to step (b).

19. The method of claim 1, wherein the oligonucleotides linked to the antibodies are at least 10 nucleotides in length.

20. The composition of claim 1, wherein the oligonucleotides linked to the antibodies are in the range of 15-200 nucleotides in length.

* * * * *